United States Patent
Ikemiya

(10) Patent No.: US 12,187,532 B2
(45) Date of Patent: Jan. 7, 2025

(54) AIR COMPOSITION ADJUSTMENT DEVICE, REFRIGERATION APPARATUS, AND TRANSPORTATION CONTAINER

(71) Applicant: DAIKIN INDUSTRIES, LTD., Osaka (JP)

(72) Inventor: Makoto Ikemiya, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 193 days.

(21) Appl. No.: 18/167,951

(22) Filed: Feb. 13, 2023

(65) Prior Publication Data

US 2023/0192395 A1 Jun. 22, 2023

Related U.S. Application Data

(63) Continuation of application No. PCT/JP2021/031994, filed on Aug. 31, 2021.

(30) Foreign Application Priority Data

Aug. 31, 2020 (JP) .................. 2020-145451

(51) Int. Cl.
*B65D 88/74* (2006.01)
*B65D 90/48* (2006.01)

(52) U.S. Cl.
CPC ........... *B65D 88/744* (2013.01); *B65D 90/48* (2013.01); *B65D 2588/743* (2013.01)

(58) Field of Classification Search
CPC .... B65D 88/744; B65D 88/745; B65D 90/48; B65D 2588/743; F24F 13/20; F24F 2110/65; F25D 11/003; F25D 2700/00; F25D 17/042; G01N 33/0009

See application file for complete search history.

(56) References Cited

U.S. PATENT DOCUMENTS

| | | | |
|---|---|---|---|
| 5,057,436 A | 10/1991 | Ball | |
| 5,457,963 A | 10/1995 | Cahill-O'Brien et al. | |
| 7,216,527 B2 | 5/2007 | Imoto | |
| 2017/0251682 A1* | 9/2017 | Kamei | ................ F25D 11/00 |
| 2020/0049645 A1 | 2/2020 | Kim et al. | |
| 2020/0253227 A1 | 8/2020 | Kamei et al. | |

FOREIGN PATENT DOCUMENTS

| | | |
|---|---|---|
| JP | 8-168 A | 1/1996 |
| JP | 2002-90325 A | 3/2002 |
| JP | 2002-195718 A | 7/2002 |
| JP | 2016-61465 A | 4/2016 |

(Continued)

OTHER PUBLICATIONS

International Search Report (PCT/ISA/210), issued in PCT/JP2021/031994, dated Oct. 12, 2021.

(Continued)

*Primary Examiner* — Emmanuel E Duke
(74) *Attorney, Agent, or Firm* — Birch, Stewart, Kolasch & Birch, LLP

(57) ABSTRACT

An air composition adjustment device is provided with a cover unit including a cover that covers around a gas sensor, an inflow path that takes air into the cover, and an outflow path that causes air to flow out from the cover.

19 Claims, 22 Drawing Sheets

(56) References Cited

FOREIGN PATENT DOCUMENTS

| | | | |
|---|---|---|---|
| JP | 2019-66169 A | 4/2019 | |
| JP | 2019148411 A * | 9/2019 | ............... A01N 3/00 |

OTHER PUBLICATIONS

Extended European Search Report for corresponding European Application No. 21861790.0, dated Nov. 29, 2023.
International Preliminary Report on Patentability and the Written Opinion of the International Searching Authority for International Application No. PCT/JP2021/031994, dated Mar. 9, 2023.

* cited by examiner

AIR COMPOSITION ADJUSTMENT DEVICE, REFRIGERATION APPARATUS, AND TRANSPORTATION CONTAINER

CROSS REFERENCE TO RELATED APPLICATIONS

This application is a Continuation of PCT International Application No. PCT/JP2021/031994, filed on Aug. 31, 2021, which claims priority under 35 U.S.C. 119 (a) to Patent Application No. 2020-145451, filed in Japan on Aug. 31, 2020, all of which are hereby expressly incorporated by reference into the present application.

TECHNICAL FIELD

The present disclosure relates to an air composition adjustment device, a refrigeration apparatus, and a transportation container.

BACKGROUND ART

Conventionally, an air composition adjustment device, configured to adjust an oxygen concentration and a carbon dioxide concentration in an internal space of a transportation container, includes a gas sensor that measures the composition of air (e.g., see Patent Document 1). In the air composition adjustment device, the concentrations of oxygen and carbon dioxide in the internal space are controlled within appropriate ranges, while measuring these concentrations by the gas sensor.

CITATION LIST

Patent Document

Patent Document 1: Japanese Unexamined Patent Publication No. H08-000168

SUMMARY

A first aspect of the present disclosure is directed to an air composition adjustment device, including: a transfer unit (31) that transfers air; an adjuster (34, 35) that adjusts the composition of air in a target space; an air circuit (3) that introduces air into the adjuster (34, 35) by the transfer unit (31) and supplies composition-adjusted air to the target space; a gas sensor (51) arranged in the target space to measure a component in air; and a cover unit (100) including a cover (101) that covers around the gas sensor (51), an inflow path (111) that takes air into the cover (101), and an outflow path (112) that causes air to flow out from the cover (101).

DESCRIPTION OF EMBODIMENTS

First Embodiment

Figure 1:
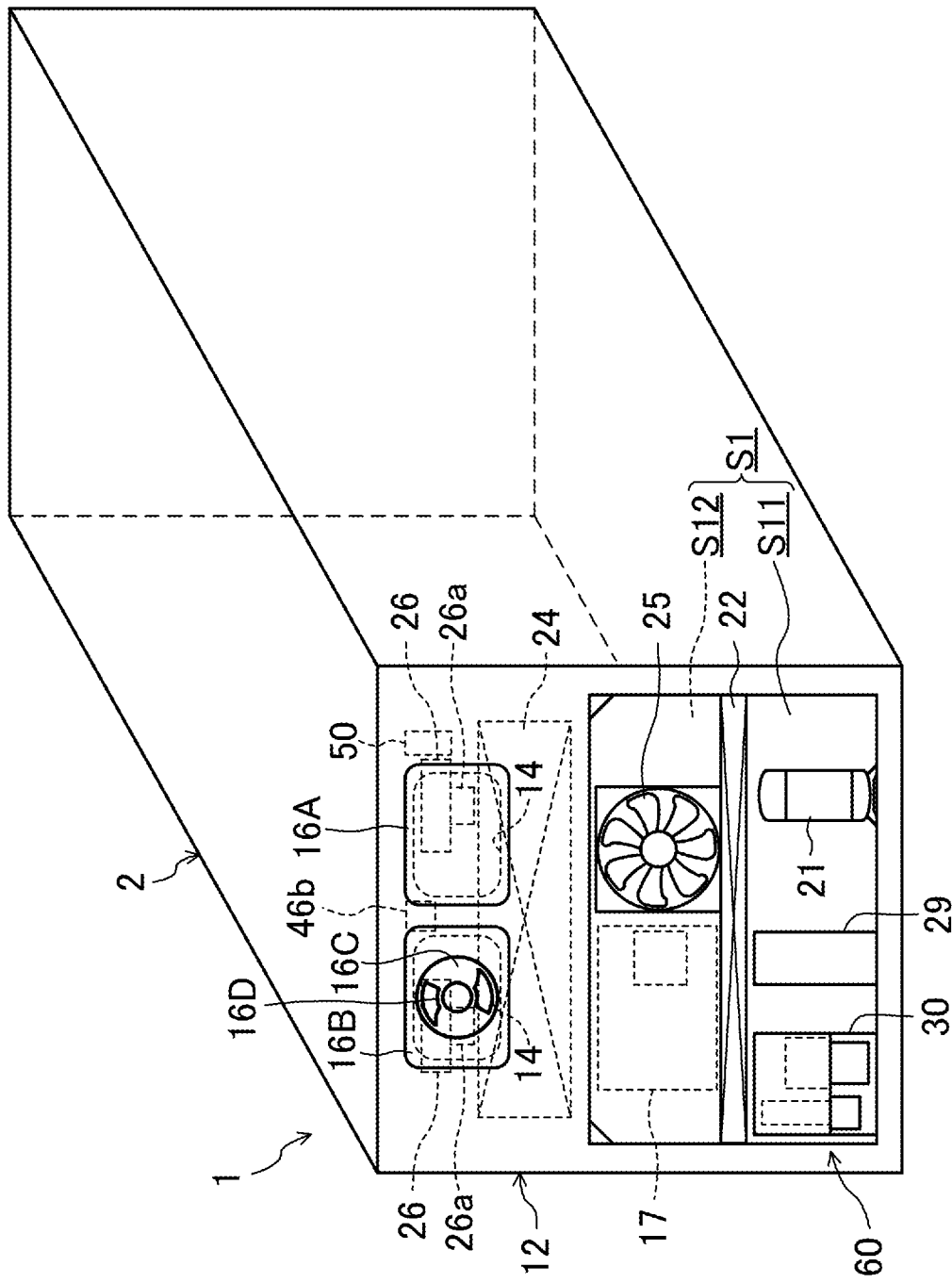
FIG. 1 is a perspective view of a transportation refrigeration apparatus according to a first embodiment of the present disclosure as viewed from the outside of a container.

A first embodiment of the present disclosure will now be described in detail with reference to the drawings.

<Entire Configuration>

This embodiment relates to a transportation container (1) including an air composition adjustment device (60) that adjusts the composition of air in a target space. The air composition adjustment device (60) includes a gas supply unit (30) and a sensor unit (50). The gas supply unit (30) includes a transfer unit (an air pump (31) to be described later) that transfers air, an adjuster (first and second adsorption columns (34, 35) to be described later) that adjusts the composition of air, and an air circuit (3) that introduces air into the adjuster by the transfer unit and supplies the composition-adjusted air to the target space. The sensor unit (50) includes sensors (51, 52) arranged in the target space to measure the composition of air.

<Transportation Container>

Figure 2:
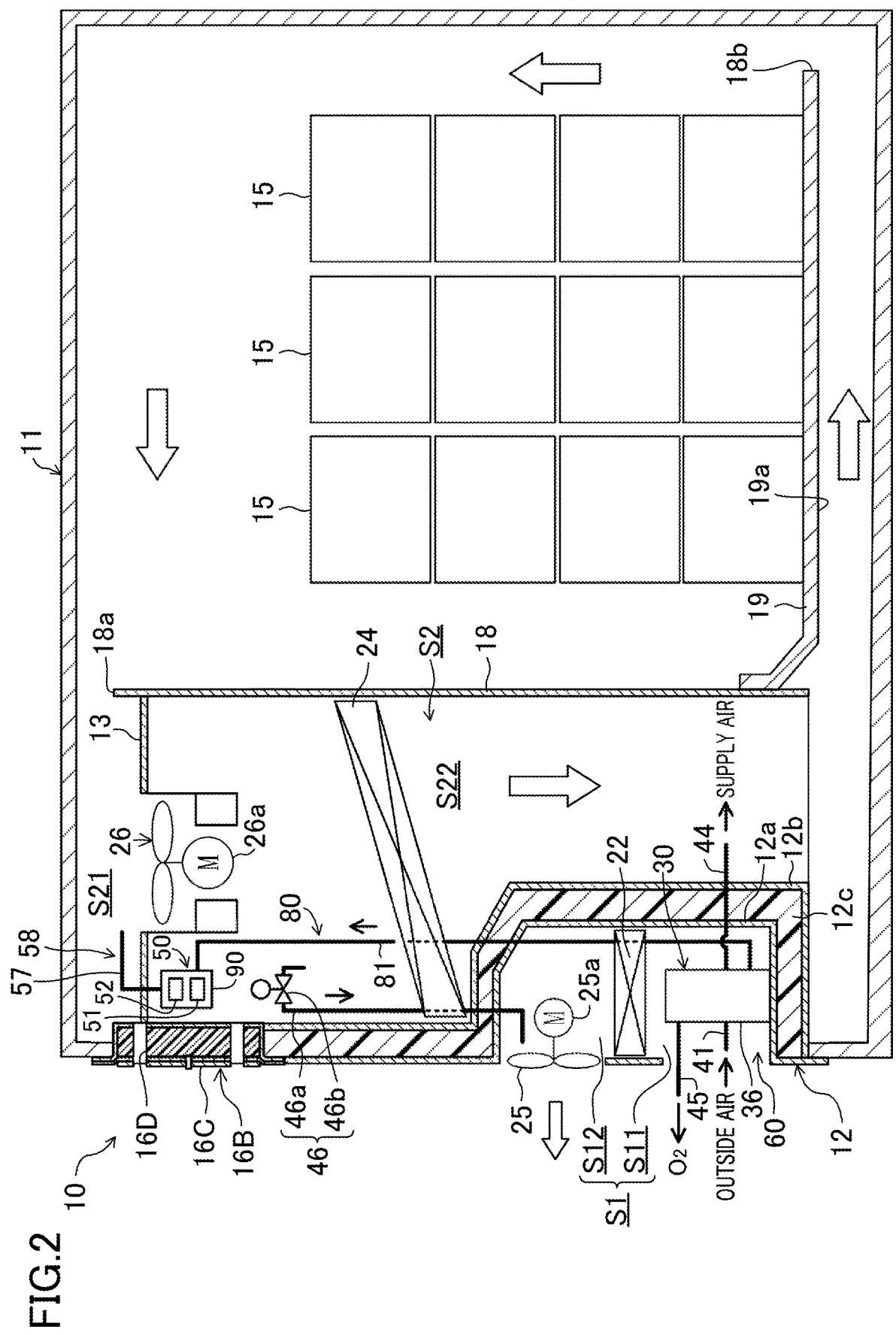
FIG. 2 is a sectional side view illustrating a schematic configuration of the transportation refrigeration apparatus of FIG. 1.

As illustrated in FIGS. 1 and 2, the transportation container (1) includes a container body (2) and a transportation refrigeration apparatus (10), and is used for, e.g., marine transportation. The transportation refrigeration apparatus (10) cools air in the container body (2) (the target space). In the internal space (the target space) of the container body (2), boxed fresh items (plants (15)) are stored. Examples of the plants (15) include fruits, vegetables, cereals, bulbous plants, and flowers, such as bananas and avocados, and the plants (15) therein breathe by absorbing oxygen (02) in air and releasing carbon dioxide ($CO_2$) into air.

The container body (2) has the shape of an elongated rectangular parallelepiped box with an open end surface. The transportation refrigeration apparatus (10) includes a casing (12), a refrigerant circuit (20), and a controller atmosphere system (an air composition adjustment device/CA system) (60). The casing (12) of the transportation refrigeration apparatus (10) is attached to close the open end of the container body (2).

<Transportation Refrigeration Apparatus>

The transportation refrigeration apparatus (10) includes the refrigerant circuit (20) that performs a refrigeration cycle, and cools air in the container body (2) by an evaporator (24) of the refrigerant circuit (20).

<Casing>

As illustrated in FIG. 2, the casing (12) of the transportation refrigeration apparatus (10) includes an external wall (12a) and an internal wall (12b), and the external wall (12a) is on an outer side and the internal wall (12b) is on an inner side with respect to the container body (2). The external wall (12a) and the internal wall (12b) are made of, for example, aluminum alloy.

The external wall (12a) is attached to a peripheral edge portion of the opening of the container body (2) so as to close the open end of the container body (2). The external wall (12a) has a lower portion protruding into the container body (2).

The internal wall (12b) is arranged to face the external wall (12a). The internal wall (12b) protrudes into the container along the lower portion of the external wall (12a). A thermal insulator (12c) fills a space between the internal wall (12b) and the external wall (12a).

As can be seen, a lower portion of the casing (12) protrudes into the container body (2). Thus, an external storage space (S1) is formed in an outer space within the lower portion of the casing (12), and an internal storage space (S2) is formed in an inner space inside an upper portion of the casing (12).

As illustrated in FIG. 1, the casing (12) includes two access openings (14) for maintenance, which are arranged side by side in a width direction of the casing (12). These two access openings (14) are each closed by openable first and second access doors (16A, 16B). The second access door (16B) includes an air vent (16D) which is closable with a rotating lid (16C) rotatable about a center axis.

As illustrated in FIG. 2, a partition plate (18) is arranged inside the container body (2). The partition plate (18) is a substantially-rectangular plate member, and is arranged to face an inner surface of the casing (12). This partition plate (18) separates the internal storage space (S2) from the internal space (the target space) of the container body (2) where the plants (15) are stored.

A suction port (18a) is formed between an upper end of the partition plate (18) and a ceiling surface in the container body (2). Air in the container body (2) is taken into the internal storage space (S2) through the suction port (18a).

A separation wall (13) extending in the horizontal direction is provided in the internal storage space (S2). The separation wall (13) is attached to an upper end portion of the partition plate (18), and has an opening in which internal fans (26) to be described later are placed. The separation wall (13) separates the internal storage space (S2) into a primary space (S21) on a suction side of the internal fans (26) and a secondary space (S22) on a blow-out side of the internal fan (26). In this embodiment, the primary space (S21) is arranged on the upper side, and the secondary space (S22) is arranged on the lower side.

In the container body (2), a floorboard (19) on which the boxed plants (15) are placed is provided above the bottom of the container body (2). An underfloor flow path (19a) is formed between the floorboard (19) and the bottom of the container body (2). There is a clearance between a lower end of the partition plate (18) and the bottom of the container body (2), and the internal storage space (S2) communicates with the underfloor flow path (19a).

A blow-out port (18b) is provided at an end of the floorboard (19) on a far side (the right side as viewed in FIG. 2) in the container body (2). Through the blow-out port (18b), air having been cooled by the transportation refrigeration apparatus (10) is blown into the container body (2).

<Configuration of Refrigerant Circuit and Arrangement of Components>

Figure 3:
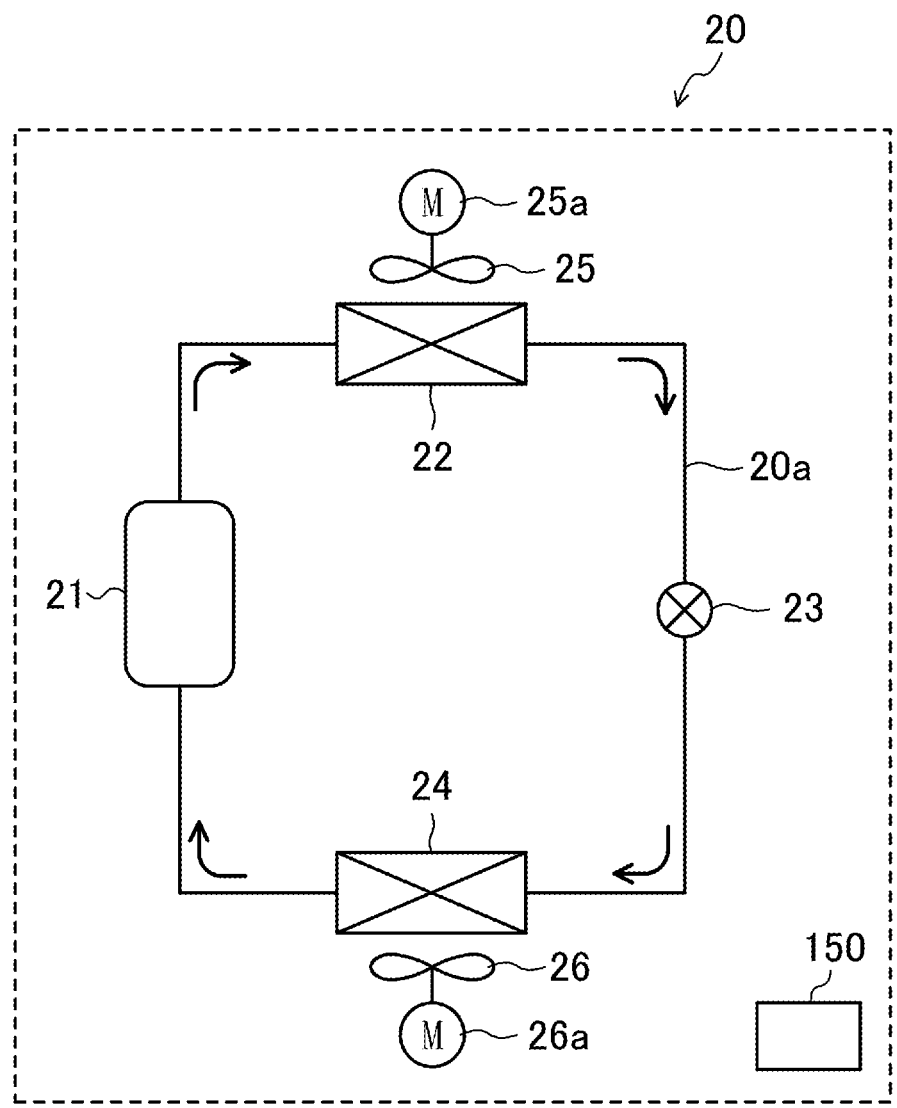
FIG. 3 is a piping system diagram illustrating a configuration of a refrigerant circuit of the transportation refrigeration apparatus of FIG. 1.

As illustrated in FIG. 3, the refrigerant circuit (20) is a closed circuit in which a compressor (21), a condenser (22), an expansion valve (23), and an evaporator (24) which are components of the refrigerant circuit (20) are connected together in this order through a refrigerant piping (20a).

In the vicinity of the condenser (22), an external fan (25) is provided. The external fan (25) is rotatably driven by an external fan motor (25a), and sends air (outside air) in the external space of the container body (2) to the condenser (22). In the condenser (22), heat is exchanged between refrigerant compressed in the compressor (21) and flowing in the condenser (22) and the outside air sent to the condenser (22) by the external fan (25).

Two internal fans (26) are provided in the vicinity of the evaporator (24). Each internal fan (26) is rotatably driven by an internal fan motor (26a), sucks air in the container body (2) through the suction port (18a), and blows the air to the evaporator (24). In the evaporator (24), heat is exchanged between refrigerant decompressed by the expansion valve (23) and flowing in the evaporator (24) and the inside air sent to the evaporator (24) by the internal fans (26).

As illustrated in FIG. 1, the compressor (21) and the condenser (22) are housed in the external storage space (S1). The condenser (22) is arranged in a middle portion of the external storage space (S1) in the vertical direction, and separates the external storage space (S1) into a lower first space (S11) and an upper second space (S12). In the first space (S11), the compressor (21), an inverter box (29) housing a driver circuit that drives the compressor (21) at a variable velocity, and the gas supply unit (30) of the CA system (60) are provided. The external fan (25) and an electric component box (17) are provided in the second space (S12).

As illustrated in FIG. 2, the evaporator (24) is housed in the secondary space (S22) of the internal storage space (S2). The above-described two internal fans (26) arranged side by side in the width direction of the casing (12) are arranged above the evaporator (24) in the internal storage space (S2) (see FIG. 1).

<Air Composition Adjustment Device>

As illustrated in FIGS. 4 to 7, the CA system (60) provided for the container body (2) includes the gas supply unit (30), an exhauster (46), the sensor unit (50), and a controller (55), and adjusts the oxygen concentration and carbon dioxide concentration of air in the container body (2). The term "concentration" to be used in the following description always indicates a "volumetric concentration."

<Gas Supply Unit>

The gas supply unit (30) is a unit that generates component-adjusted air to be supplied into the container body (2). In this embodiment, the gas supply unit (30) is a unit that generates nitrogen-enriched air having a low oxygen concentration, which is to be supplied into the container body (2). In this embodiment, the gas supply unit (30) employs vacuum pressure swing adsorption (VPSA). As illustrated in FIG. 1, the gas supply unit (30) is arranged at a lower left corner of the external storage space (S1).

Figure 4:
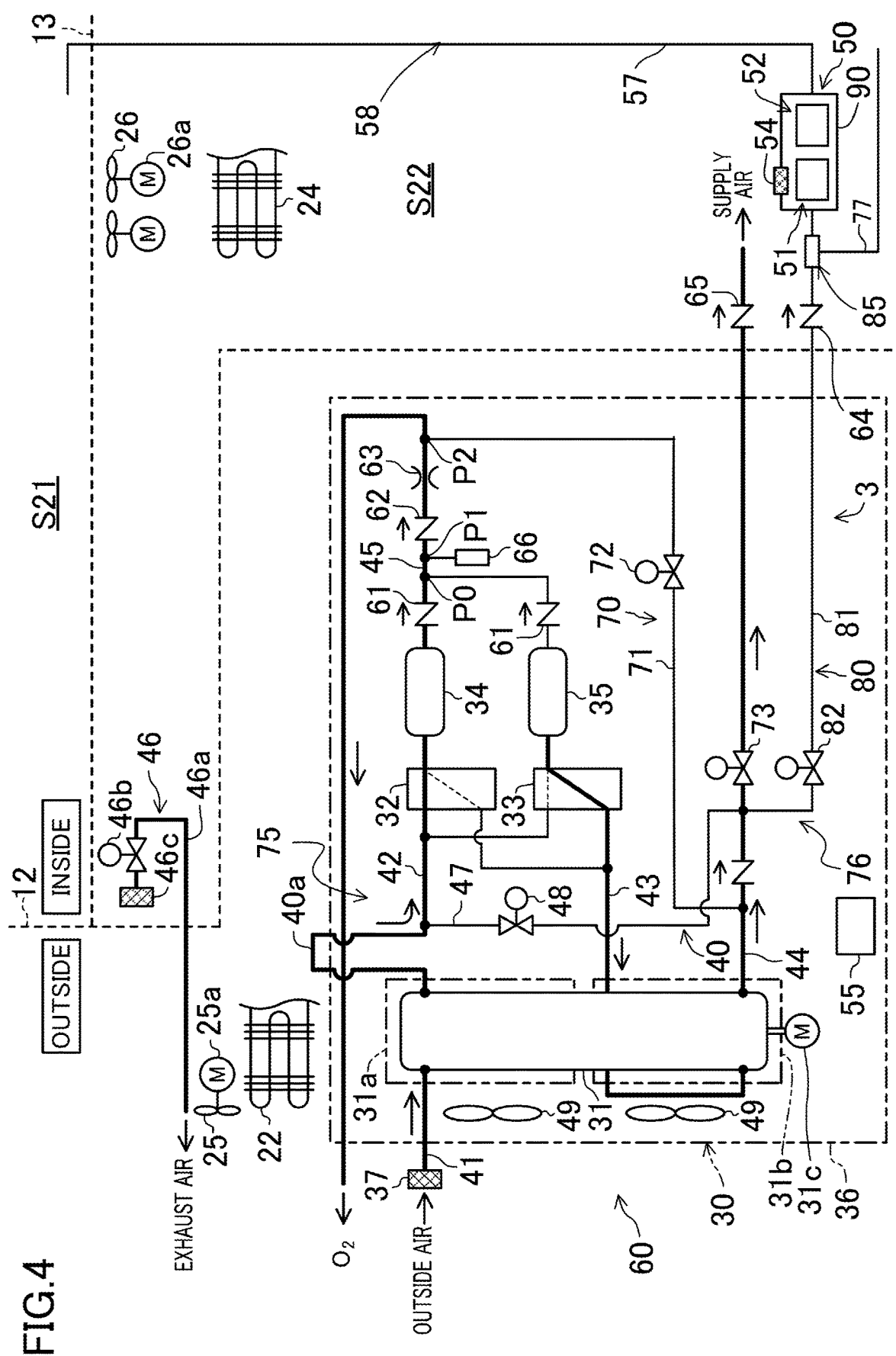
FIG. 4 is a piping system diagram illustrating an air circuit of a CA system of the transportation refrigeration apparatus of FIG. 1, which illustrates the flow of air in a first operation.

As illustrated in FIG. 4, the gas supply unit (30) has the air circuit (3) in which the air pump (31), first and second directional control valves (32, 33), and the first and second adsorption columns (34, 35) each provided with an adsorbent for adsorbing a nitrogen component in air are connected together. The components of the air circuit (3) are housed in a unit case (36).

(Air Pump)

The air pump (31) has a first pump mechanism (a compression pump mechanism) (31a) and a second pump mechanism (a decompression pump mechanism) (31b), each of which sucks air, compresses the air, and discharges the compressed air. The first pump mechanism (31a) and the second pump mechanism (31b) are connected to a drive shaft of a motor (31c).

(Air Circuit)

The air circuit (3) in which the components such as the air pump (31) are connected together includes an outside air passage (41), a compression passage (42), a decompression passage (43), and a supply passage (44).

One end of the outside air passage (41) penetrating the unit case (36) from the inside to the outside thereof is connected to a suction port of the first pump mechanism (31a). An air-permeable, waterproof membrane filter (37) is provided at the other end of the outside air passage (41). Although not shown in the figure, the other end of the outside air passage (41) where the membrane filter (37) is provided is arranged in the second space (S12) of the external storage space (51) above the condenser (22).

One end of the compression passage (42) is connected to a discharge port of the first pump mechanism (31a). The other end of the compression passage (42) is divided into two branches, which are connected to the first and second directional control valves (32, 33), respectively.

One end of the decompression passage (43) is connected to a suction port of the second pump mechanism (31b). The other end of the decompression passage (43) is divided into two branches, which are connected to the first and second directional control valves (32, 33), respectively. One end of the supply passage (44) is connected to a discharge port of the second pump mechanism (31b). The other end of the supply passage (44) opens to the secondary space (S22) on the blow-out side of the internal fans (26) in the internal storage space (S2) of the container body (2). The supply passage (44) is provided with a check valve (65) at the other end portion thereof, the check valve (65) allowing air to flow toward the internal storage space (S2) and preventing backflow of the air.

Two blower fans (49) are provided on the lateral side of the air pump (31), the blower fans (49) cooling the air pump (31) by blowing air to the air pump (31).

The first pump mechanism (31a), which serves as the compression pump mechanism, performs an adsorption operation in which a nitrogen component in compressed air adsorbs to the adsorbent in one adsorption column (34, 35) by supplying the compressed air to the one adsorption column (34, 35). The second pump mechanism (31b), which serves as the decompression pump mechanism, performs a desorption operation (an operation of generating nitrogen-enriched air) in which a nitrogen component on the adsorbent in the other adsorption column (34, 35) is desorbed by sucking air from the other adsorption column (34, 35).

The supply passage (44) is a passage through which nitrogen-enriched air generated by the desorption operation while the adsorption operation and the desorption operation are performed alternately for the adsorption columns (34, 35) is supplied into the container body (2).

An outlet (a portion between the compression pump mechanism (31a) and the directional control valve (32, 33)) of the compression pump mechanism (31a) in the compression passage (42) and an outlet of the decompression pump mechanism (31b) in the supply passage (44) are connected to each other through a bypass passage (47). The bypass passage (47) is provided with a bypass on-off valve (48), opening or closing of which is controlled by the controller (55).

An outside air introduction passage (40) is formed of the outside air passage (41), part of the compression passage (42), the bypass passage (47) having the bypass on-off valve (48), and part of the supply passage (44). The outside air introduction passage (40) supplies, into the container, compressed air (air having the same composition as that of outside air) having passed through the compression pump mechanism (31a). The outside air introduction passage (40) is provided with a cooling portion (40a) passing through a space outside the unit case (36).

(Directional Control Valve)

The first and second directional control valves (32, 33) are provided for the air circuit (3), and each valve (32, 33) is arranged between the air pump (31) and a corresponding one of the first and second adsorption columns (34, 35). The first and second directional control valves (32, 33) switch the state of connection between the air pump (31) and the first or second adsorption column (34, 35) between two connection states (first and second connection states) to be described later. The controller (55) controls such a switching operation.

The first directional control valve (32) is connected to the compression passage (42) connected to the discharge port of the first pump mechanism (31a), the decompression passage (43) connected to the suction port of the second pump mechanism (31b), and one end portion (an inflow port in compression) of the first adsorption column (34). The first directional control valve (32) switches between a first state (a state illustrated in FIG. 4) in which the first adsorption column (34) communicates with the discharge port of the first pump mechanism (31a) and is blocked from the suction port of the second pump mechanism (31b) and a second state (a state illustrated in FIG. 5) in which the first adsorption column (34) communicates with the suction port of the second pump mechanism (31b) and is blocked from the discharge port of the first pump mechanism (31a).

The second directional control valve (33) is connected to the compression passage (42) connected to the discharge port of the first pump mechanism (31a), the decompression passage (43) connected to the suction port of the second pump mechanism (31b), and one end portion of the second adsorption column (35). The second directional control valve (33) switches between a first state (a state illustrated in FIG. 4) in which the second adsorption column (35) communicates with the suction port of the second pump mechanism (31b) and is blocked from the discharge port of the first pump mechanism (31a) and a second state (a state illustrated in FIG. 5) in which the second adsorption column (35) communicates with the discharge port of the first pump mechanism (31a) and is blocked from the suction port of the second pump mechanism (31b).

If the first and second directional control valves (32, 33) are both set to the first state, the air circuit (3) is switched to the first connection state (see FIG. 4). In the first connection state, the discharge port of the first pump mechanism (31a) is connected to the first adsorption column (34), and the suction port of the second pump mechanism (31b) is connected to the second adsorption column (35). In this state, the adsorption operation is performed on the first adsorption column (34) to adsorb the nitrogen component in the outside air to the adsorbent, and the desorption operation is performed on the second adsorption column (35) to desorb the nitrogen component on the adsorbent.

Figure 5:
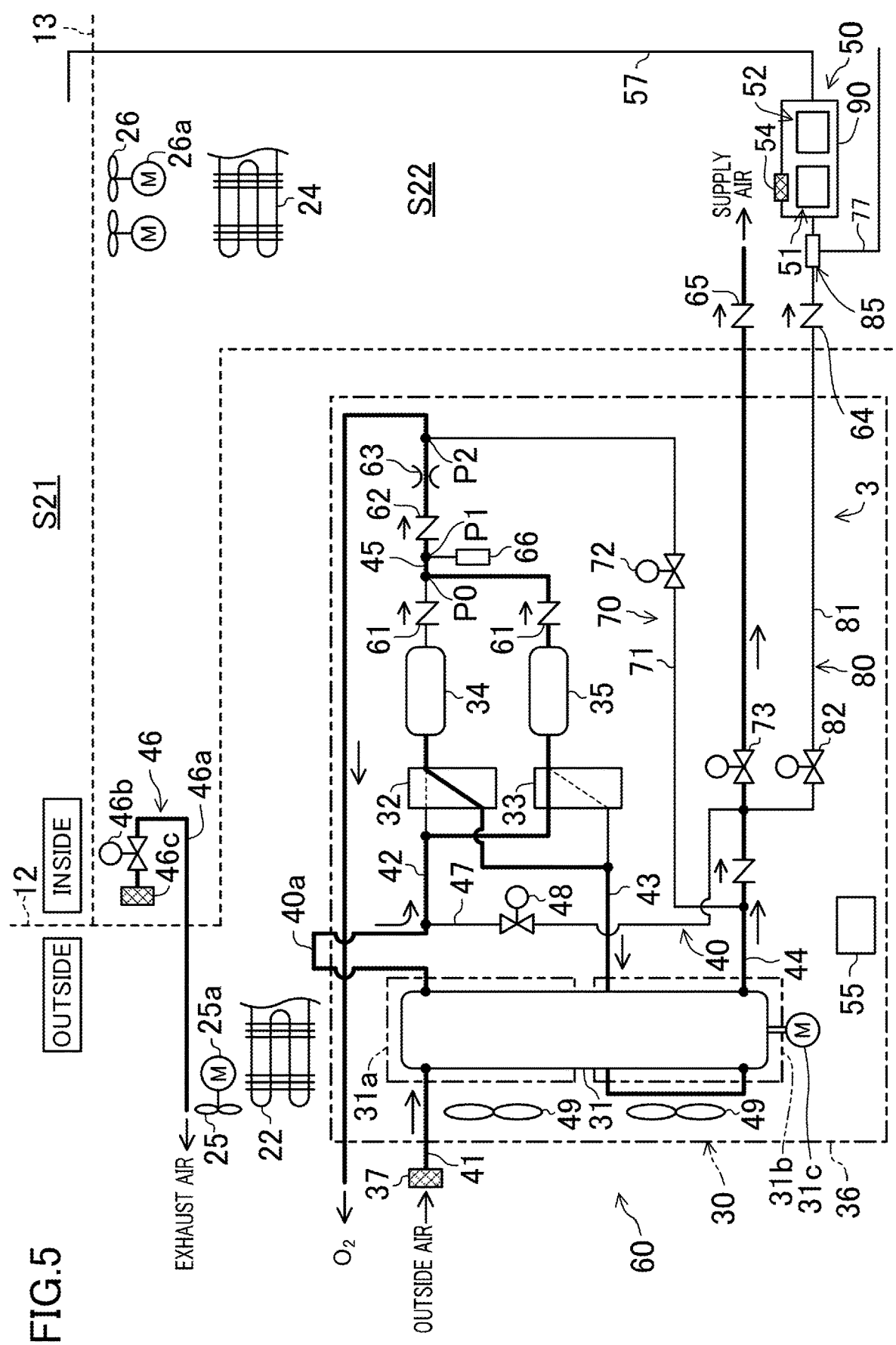
FIG. 5 is a piping system diagram illustrating the air circuit of the CA system of the transportation refrigeration apparatus of FIG. 1, which illustrates the flow of air in a second operation.
Figure 6:
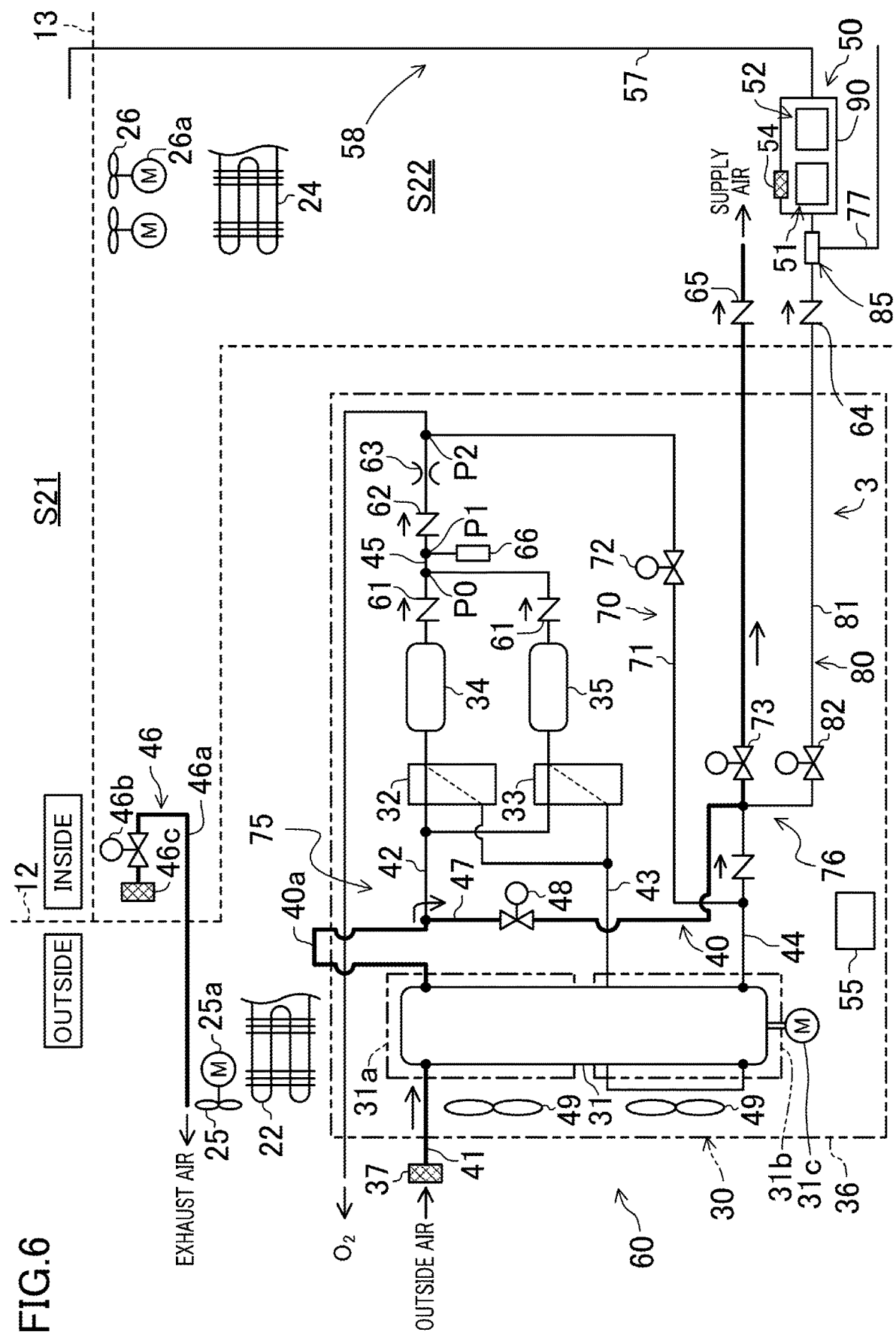
FIG. 6 is a piping system diagram illustrating the air circuit of the CA system of the transportation refrigeration apparatus of FIG. 1, which illustrates the flow of air in an outside air introduction operation.

If the first and second directional control valves (32, 33) are both set to the second state, the air circuit (3) is switched to the second connection state (see FIG. 5). In the second connection state, the discharge port of the first pump mechanism (31a) is connected to the second adsorption column (35), and the suction port of the second pump mechanism (31b) is connected to the first adsorption column (34). In this state, the adsorption operation is performed on the second adsorption column (35), and the desorption operation is performed on the first adsorption column (34).

(Adsorption Column)

The first and second adsorption columns (34, 35) are cylindrical members filled with the adsorbent. The adsorbent filling the first and second adsorption columns (34, 35) adsorbs the nitrogen component under a condition where the adsorption column (34, 35) is compressed, and desorbs the nitrogen component under a condition where the adsorption column (34, 35) is decompressed.

The adsorbent filling the first and second adsorption columns (34, 35) is porous zeolite having pores with diameters being smaller than the diameter of nitrogen molecules (3.0 angstrom) but greater than the diameter of oxygen molecules (2.8 angstrom), for example. With the use of zeolite having such pore diameters as the adsorbent, the nitrogen component in the air can be adsorbed.

If the air pump (31) supplies the compressed outside air to the first and second adsorption columns (34, 35) to compress the inside of these columns (34, 35), the nitrogen component in the outside air adsorbs to the adsorbent. This generates oxygen-enriched air that has had its nitrogen concentration lowered and oxygen concentration increased by including less nitrogen component than the outside air does. On the other hand, if the air pump (31) sucks air from the first and second adsorption columns (34, 35) to decompress the inside of these columns (34, 35), the nitrogen component on the adsorbent is desorbed. This generates nitrogen-enriched air that has had its nitrogen concentration increased and oxygen concentration lowered by including more nitrogen component than the outside air does. In this embodiment, nitrogen-enriched air of 92% nitrogen and 8% oxygen, for example, is generated.

The respective other end portions (outflow ports in compression) of the first and second adsorption columns (34, 35) are connected to one end of an oxygen discharge passage (45) through which the oxygen-enriched air that has been generated from the compressed outside air is guided toward the outside of the container body (2). The one end of the oxygen discharge passage (45) is divided into two branches, which are connected to the other end portions of the first and second adsorption columns (34, 35), respectively. The other end of the oxygen discharge passage (45) opens outside the gas supply unit (30), i.e., outside the container body (2). The branches of the oxygen discharge passage (45) are connected to the first and second adsorption columns (34, 35), respectively. Each of these junction portions is provided with a check valve (61) that prevents backflow of the air from the oxygen discharge passage (45) toward the first and second adsorption columns (34, 35).

A check valve (62) and an orifice (63) are provided in this order at some midpoints of the oxygen discharge passage (45) from one end to the other end thereof. The check valve (62) prevents backflow of the nitrogen-enriched air from an exhaust connection passage (71) to be described later toward the first and second adsorption columns (34, 35). The orifice (63) decompresses the oxygen-enriched air having flowed out of the first and second adsorption columns (34, 35) before the oxygen-enriched air is discharged to the outside of the container.

The oxygen discharge passage (45) through which the oxygen-enriched air is discharged to the outside of the container from the adsorption columns (34, 35) is provided with a pressure sensor (66). The pressure sensor (66) is arranged between a confluence (P0) between the first and second adsorption columns (34, 35) and the check valve (62).

The exhaust connection passage (71) is a passage connecting the discharge port of the decompression pump mechanism (31b) to the oxygen discharge passage (45) in the downstream of the pressure sensor (66). The check valve (62) is provided between a first connecting point (P1) where the pressure sensor (66) and the oxygen discharge passage (45) are connected together and a second connecting point (P2) where the oxygen discharge passage (45) and the exhaust connection passage (71) are connected together. The check valve (62) allows the air to flow from the first connecting point (P1) to the second connecting point (P2), and prevents the air from flowing in the reverse direction.

(Supply-Discharge Switching Mechanism)

The air circuit (3) is provided with a supply-discharge switching mechanism (70) that switches between a gas supply operation and a gas discharge operation. The gas supply operation is an operation in which the nitrogen-enriched air is supplied from the first and second adsorption columns (34, 35) into the container body (2). The gas discharge operation is an operation in which the nitrogen-enriched air is discharged from the first and second adsorption columns (34, 35) to the outside of the container. The supply-discharge switching mechanism (70) includes the exhaust connection passage (71), an exhaust on-off valve (72), and a supply on-off valve (73).

The exhaust connection passage (71) has one end connected to the supply passage (44) and the other end connected to the oxygen discharge passage (45). The other end of the exhaust connection passage (71) is connected to the oxygen discharge passage (45) so as to be located further toward the outside of the container than the orifice (63).

The exhaust on-off valve (72) is provided on the exhaust connection passage (71). The exhaust on-off valve (72) is an electromagnetic valve on an intermediate portion of the exhaust connection passage (71). The exhaust on-off valve (72) switches between an open state in which the flow of the nitrogen-enriched air having flowed in from the supply passage (44) is allowed and a closed state in which the flow of the nitrogen-enriched air is blocked. The controller (55) controls opening and closing of the exhaust on-off valve (72).

The supply on-off valve (73) is provided on the supply passage (44) so as to be arranged further toward the inside of the container than the junction where the supply passage (44) and the exhaust connection passage (71) are connected together. The supply on-off valve (73) is an electromagnetic valve which switches between an open state in which the flow of air into the container is allowed and a closed state in which the flow of air into the container is blocked. The controller (55) controls opening and closing of the supply on-off valve (73).

<Exhauster>

As illustrated in FIGS. 2 and 4, the exhauster (46) has an exhaust passage (46a) connecting the internal storage space (S2) and the external space together, an exhaust valve (46b) connected to the exhaust passage (46a), and a membrane filter (46c) provided at an inlet end (an end portion inside the container) of the exhaust passage (46a). The exhaust passage (46a) penetrates the casing (12) from the inside to the outside thereof. The exhaust valve (46b) is provided on the exhaust passage (46a) inside the container. The exhaust valve (46b) is an electromagnetic valve which switches between an open state in which the flow of air in the exhaust passage (46a) is allowed and a closed state in which the flow of air in the exhaust passage (46a) is blocked. The controller (55) controls opening and closing of the exhaust valve (46b).

When the controller (55) opens the exhaust valve (46b) during rotation of the internal fans (26), an exhaust operation in which air (inside air) in the internal storage space (S2) communicating with the internal space is discharged to the outside of the container is performed.

More specifically, when the internal fans (26) rotate, the pressure of the secondary space (S22) on the blow-out side becomes higher than the pressure of the external space (i.e., an atmospheric pressure). Thus, when the exhaust valve (46b) is in the open state, air (inside air) in the internal storage space (S2) communicating with the internal space is discharged to the external space through the exhaust passage (46a) due to a pressure difference (a pressure difference between the external space and the secondary space (S22)) between both ends of the exhaust passage (46a).

<Circuit Configuration of Sensor Unit>

As illustrated in FIGS. 2 and 4, the sensor unit (50) is provided in the secondary space (S22) on the blow-out side of the internal fans (26) in the internal storage space (S2). The sensor unit (50) has an oxygen sensor (51), a carbon dioxide sensor (52), a membrane filter (54), and an exhaust piping (57). The oxygen sensor (51) and the carbon dioxide sensor (52) are housed in a sensor casing (90). The sensor casing (90) includes a later-described introduction port (94) through which air is introduced into the sensor casing (90), and the membrane filter (54) in FIG. 4 is attached to the introduction port (94).

The oxygen sensor (51) is a zirconia sensor. The carbon dioxide sensor (52) is a non-dispersive infrared (NDIR) sensor. One end of the exhaust piping (57) is coupled to the sensor casing (90), and the other end of the exhaust piping (57) opens in the vicinity of the suction ports of the internal fans (26).

The secondary and primary spaces (S22, S21) of the internal storage space (S2) communicate with each other through a communication passage (58) including the membrane filter (54), the oxygen sensor (51), the carbon dioxide sensor (52), and the exhaust piping (57). During operation of the internal fans (26), the pressure of the primary space (S21) is lower than the pressure of the secondary space (S22). Due to this pressure difference, the inside air flows from the secondary space (S22) toward the primary space (S21) in the communication passage (58) including the oxygen sensor (51) and the carbon dioxide sensor (52). Thus, during operation of the internal fans (26), the inside air passes through the oxygen sensor (51) and the carbon dioxide sensor (52) as described above, and meanwhile, the oxygen concentration of the inside air is measured by the oxygen sensor (51) and the carbon dioxide concentration of the inside air is measured by the carbon dioxide sensor (52).

The air circuit (3) is provided with a sensor circuit (80) that performs a later-described supply air measurement operation in which the concentration of the nitrogen-enriched air generated by the first and second adsorption columns (34, 35) is measured using the oxygen sensor (a gas sensor of the present disclosure) (51). The sensor circuit (80) includes a branch piping (81) and a branch on-off valve (a gas concentration measurement on-off valve) (82), and allows part of air flowing in the supply passage (44) to be diverged toward the oxygen sensor (51) and the carbon dioxide sensor (52).

One end of the branch piping (81) is connected to the supply passage (44), and the other end of the branch piping (81) is connected to the sensor casing (90). The branch piping (81) is branched from the supply passage (44) in the unit case (36), and communicates with the internal space. The branch piping (81) is provided with a check valve (64) at the other end portion thereof (a portion inside the container). The check valve (64) allows the flow of air from one end to the other end of the branch piping (81), and prevents backflow of the air.

The branch on-off valve (82) is provided in the unit case (36). The branch on-off valve (82) is an electromagnetic valve which switches between an open state in which the flow of air in the branch piping (81) is allowed and a closed state in which the flow of air in the branch piping (81) is blocked. The controller (55) controls opening and closing of the branch on-off valve (82).

When the supply air measurement operation is performed during the stop of operation of the internal fans (26), the nitrogen-enriched air generated in the gas supply unit (30) is guided to the oxygen sensor (51) through the branch piping (81), and the oxygen concentration of the nitrogen-enriched air is measured by the oxygen sensor (51).

In the air composition adjustment device, when the measurement value of the sensor deviates from an actual value, adjustment of the concentration becomes unstable, and for this reason, outside air is introduced into the gas sensor (51) at a predetermined timing to calibrate the gas sensor (51) (correct the measurement value). During calibration of the oxygen sensor (51), the outside air compressed in the air pump (31) bypasses the first and second adsorption columns (34, 35), passes through the branch piping (81), and is introduced into the oxygen sensor (51), as described later.

In order to introduce the outside air into the oxygen sensor (51), the air circuit (3) has a first passage (75) (the outside air passage (41) and the compression passage (42)) for introducing the outside air into the first and second adsorption columns (34, 35) by the air pump (31) and a second passage (76) (the bypass passage (47) and the branch piping (81)) being branched from the first passage (41, 42) between the air pump (31) and the first and second adsorption columns (34, 35) and communicating with the oxygen sensor (51).

The second passage (76) is provided with a gas-liquid separator (85) that removes moisture from the air introduced into the oxygen sensor (51). A drain piping (77) through which the moisture separated from the air is drained is connected to the gas-liquid separator (85).

Next, the arrangement and structure of the sensor casing (90) will be described.

(Arrangement and Structure of Sensor Unit)

Figure 8:
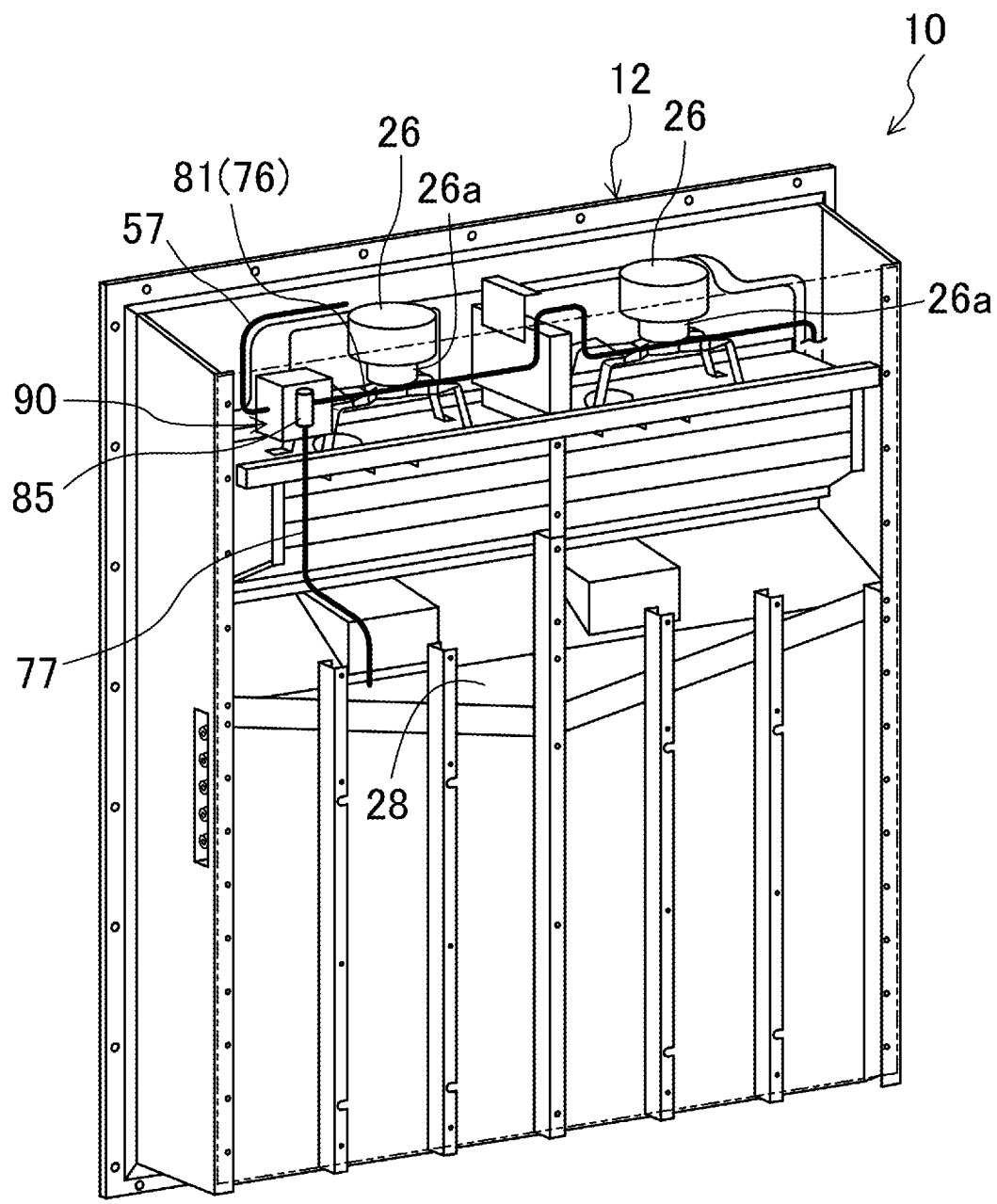
FIG. 8 is a perspective view of the rear side of a casing of the transportation refrigeration apparatus, which illustrates arrangement of a sensor unit.
Figure 9:
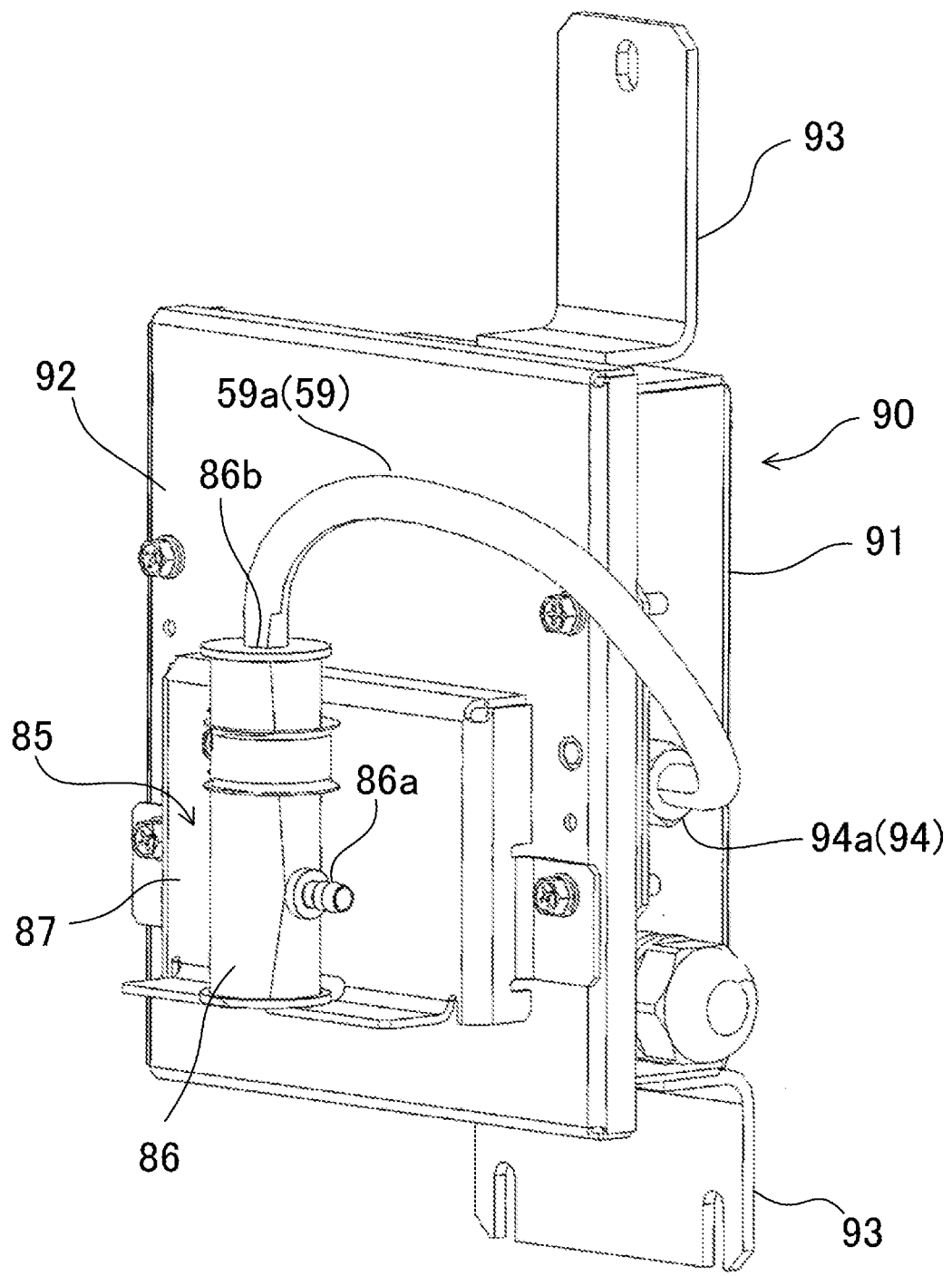
FIG. 9 is a perspective view of the sensor unit.
Figure 10:
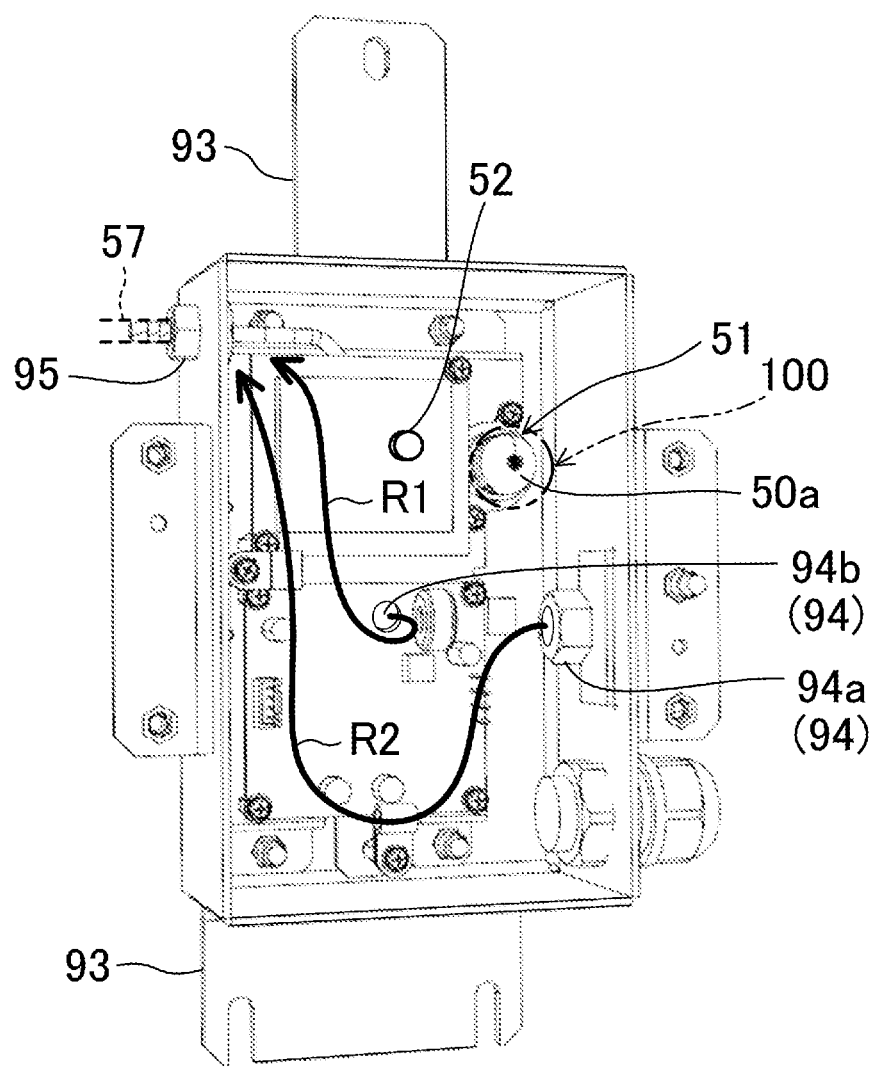
FIG. 10 is a perspective view illustrating the inside of the sensor unit.
Figure 11:
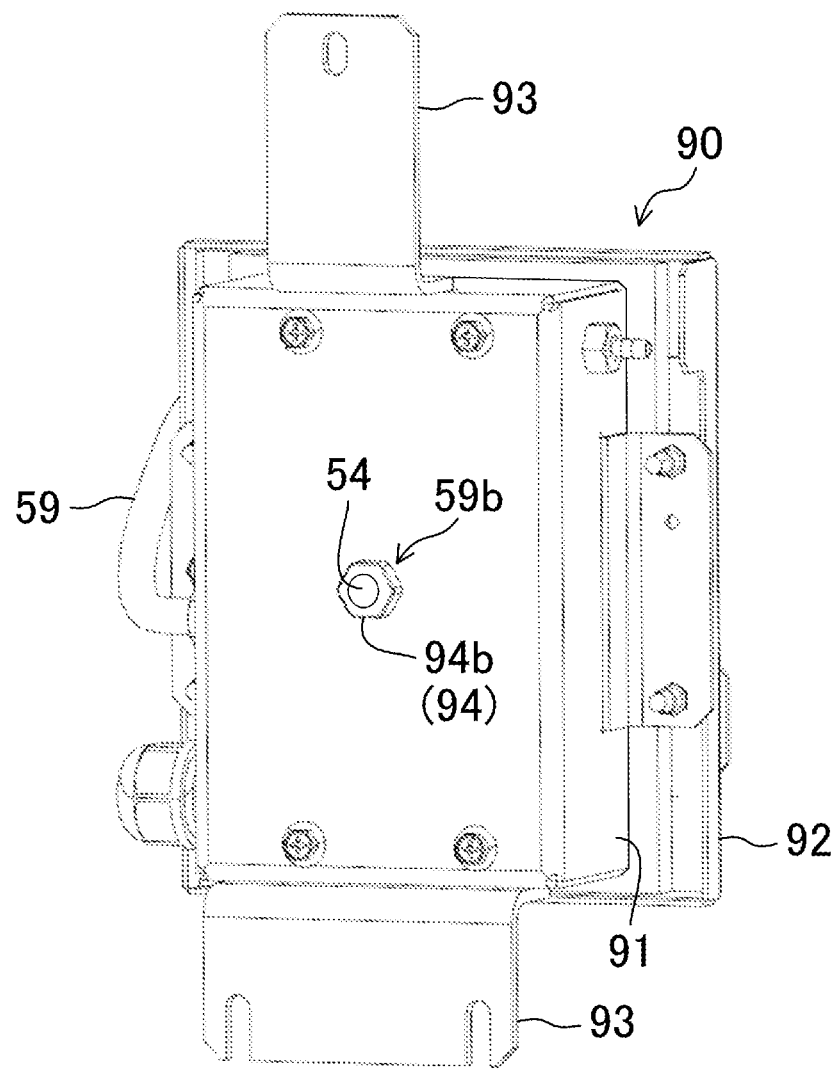
FIG. 11 is a perspective view of the sensor unit viewed from behind.
Figure 12:
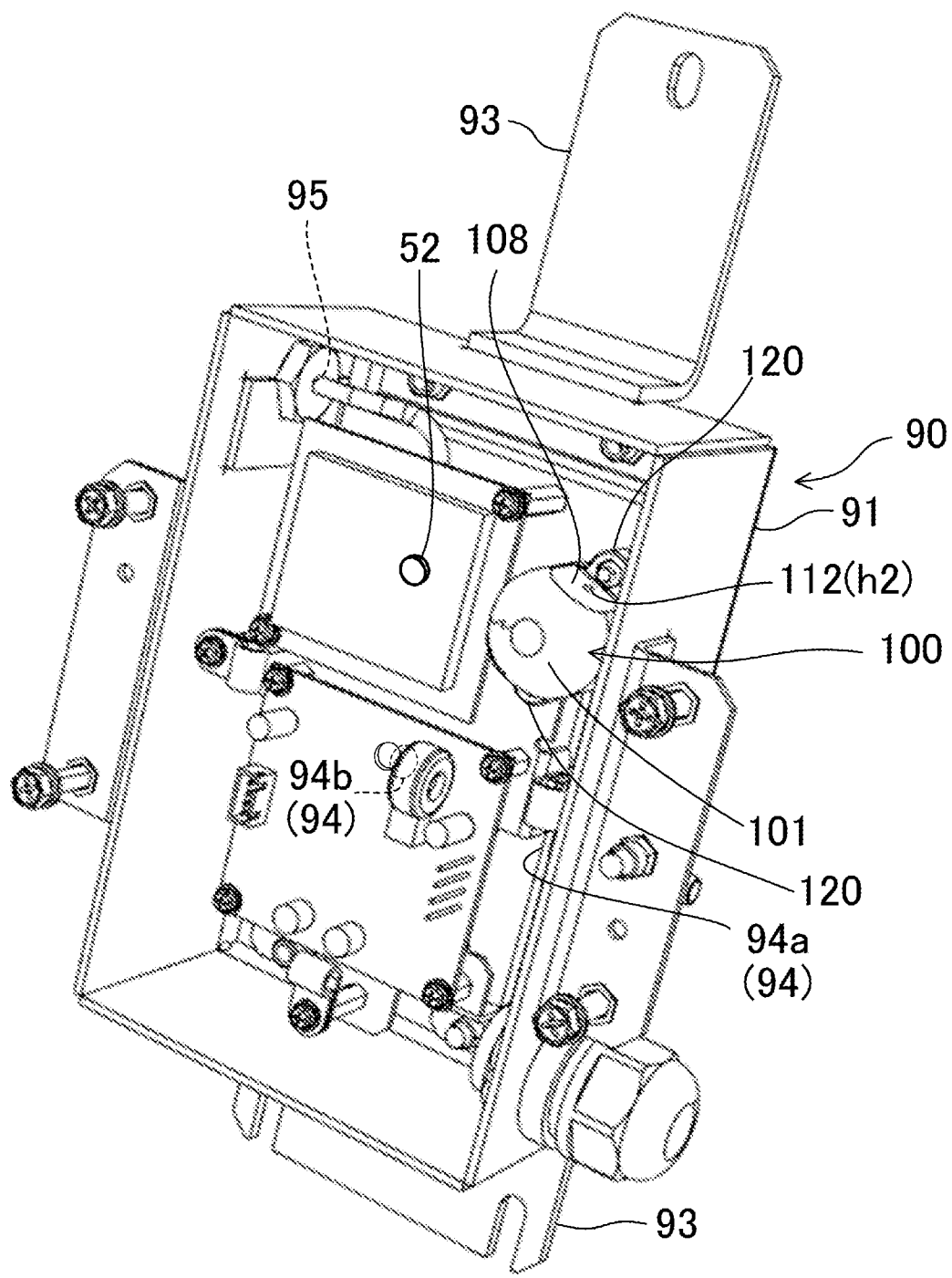
FIG. 12 is a perspective view illustrating the inside of the sensor unit.

FIG. 8 is a perspective view of the rear side of the casing (12) of the transportation refrigeration apparatus (10), which illustrates arrangement of the sensor casing (90). FIG. 9 is an enlarged perspective view of the sensor casing (90). FIG. 10 is a perspective view illustrating the inside of the sensor casing (90), which indicates a cover unit of the oxygen sensor by a virtual line. FIG. 11 is a perspective view of the sensor casing (90) as viewed from the rear side thereof. FIG. 12 is another perspective view illustrating the inside of the sensor casing (90). In FIG. 10, a cover unit (100) to be described in detail later is indicated by a dashed line.

As described above, the oxygen sensor (51) and the carbon dioxide sensor (52) are housed in the sensor casing (90). The gas-liquid separator (85) is fixed to the sensor casing (90). As illustrated in FIG. 9, the gas-liquid separator (85) has a tubular container (86). The container (86) of the gas-liquid separator (85) has an inflow port (86a) through which air flows into the container (86), an outflow port (86b) through which air, from which (part of) moisture has been removed, flows out of the container (86), and a drain port (not shown) through which the moisture separated from the air is discharged.

In FIG. 8, the branch piping (81), which is part of the second passage (76), is connected to the inflow port (86a) of the gas-liquid separator (85) fixed to the sensor casing (90). The drain piping (77) connected to the gas-liquid separator (85) extends downward from the gas-liquid separator (85) such that moisture is discharged to a drain pan (28) provided for the casing (12) to receive drain water generated in the transportation refrigeration apparatus (10). The exhaust piping (57) connected to the sensor casing (90) opens on the suction port side of the internal fans (26).

The sensor casing (90) has a sensor casing body (91) and a case cover (92). The gas-liquid separator (85) is fixed to the case cover (92) of the sensor casing (90) with a bracket (87). The sensor casing (90) is fixed to the casing (12) of the transportation refrigeration apparatus (10) with a bracket (93). In this embodiment, the sensor casing (90) is positioned in the internal storage space (S2).

The sensor casing (90) includes the introduction port (94) for introducing air into the sensor casing (90) and an ejection port (95) for ejecting air to the outside of the sensor casing (90). The introduction port (94) includes a first introduction port (94a) and a second introduction port (94b). The first introduction port (94a) is an opening through which air outside the internal space is introduced into the sensor casing (90). The second introduction port (94b) is an opening through which air inside the internal space is introduced into the sensor casing (90).

As illustrated in FIGS. 9 and 10, the first introduction port (94a) is provided at a side surface of the sensor casing (90), and the branch piping (81) (the second passage (76)) is connected thereto. As illustrated in FIG. 11, the second introduction port (94b) is provided at a rear surface of the sensor casing (90), and opens to the internal space. The membrane filter (54) allowing air to pass therethrough, but blocking moisture is attached to each of the first introduction port (94a) and the second introduction port (94b). The membrane filter (54) is provided at a ventilation hole of a hexagonal fastening member. The exhaust piping (57) is connected to the ejection port (95).

Both the first introduction port (94a) and the second introduction port (94b) are arranged below the oxygen sensor (51).

The outflow port (86b) of the gas-liquid separator (85) and the first introduction port (94a) are connected together through a connection piping (59). The connection piping (59) forms a first introduction path (59a) for supplying air from the air pump (31) into the sensor casing (90). The second introduction port (94b) for introducing the inside air into the sensor casing (90) forms a second introduction path (59b).

<Details of Cover Unit Oxygen Sensor>

The air composition adjustment device (60) includes the cover unit (100). The cover unit (100) covers around the oxygen sensor (51). The cover unit (100) is made of a resin material. The cover unit (100) is a synthetic resin molded component. The cover unit (100) reduces contact of a corrosive component (e.g., sulfur) in air with the oxygen sensor (51). The corrosive component is assumed to be generated from a cardboard box in the container packed with the boxed plants or a wood pallet on which the cardboard box is placed or to be contained in the outside air.

Figure 13:
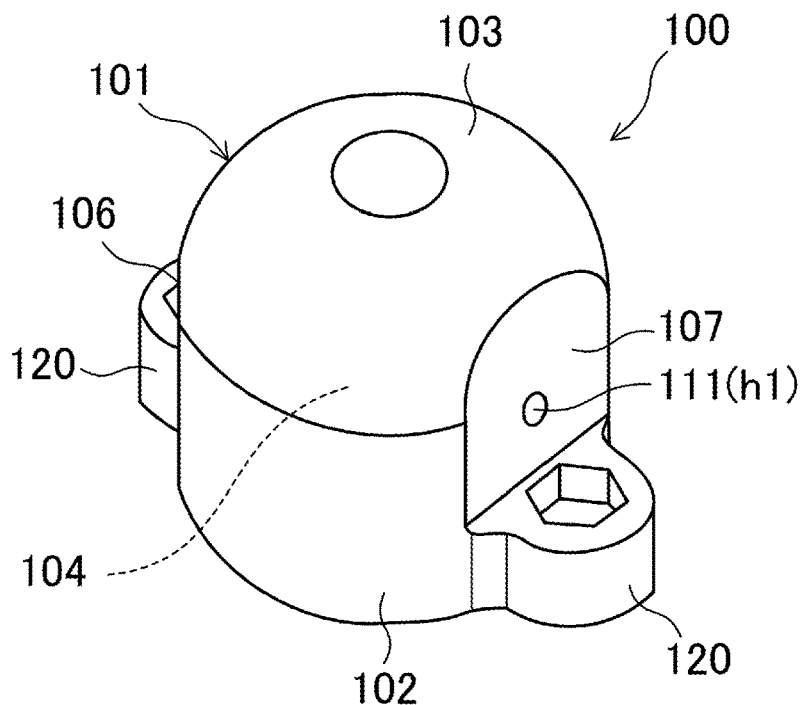
FIG. 13 is a perspective view schematically illustrating a cover unit.
Figure 14:
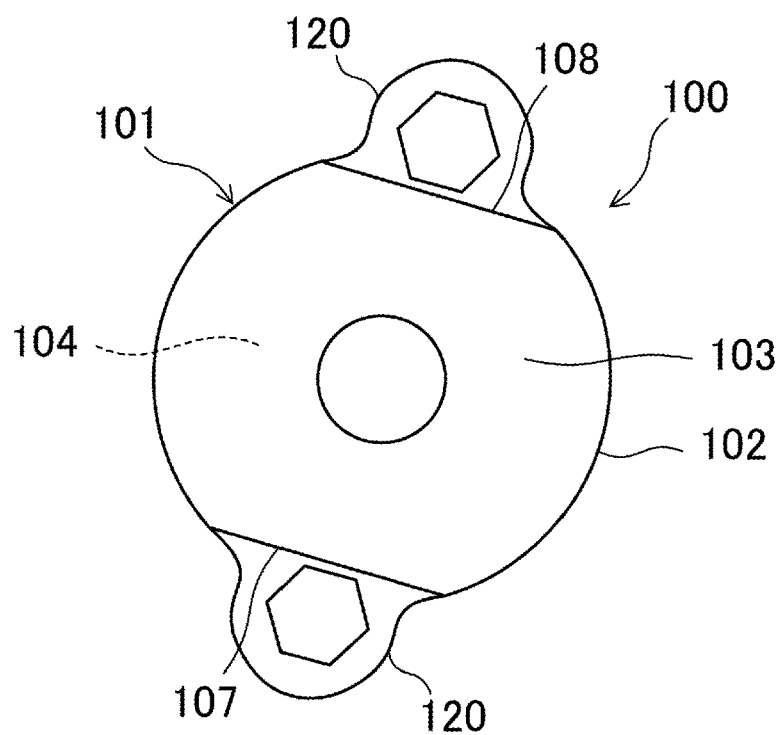
FIG. 14 is a view of the cover unit as viewed from above.
Figure 15:
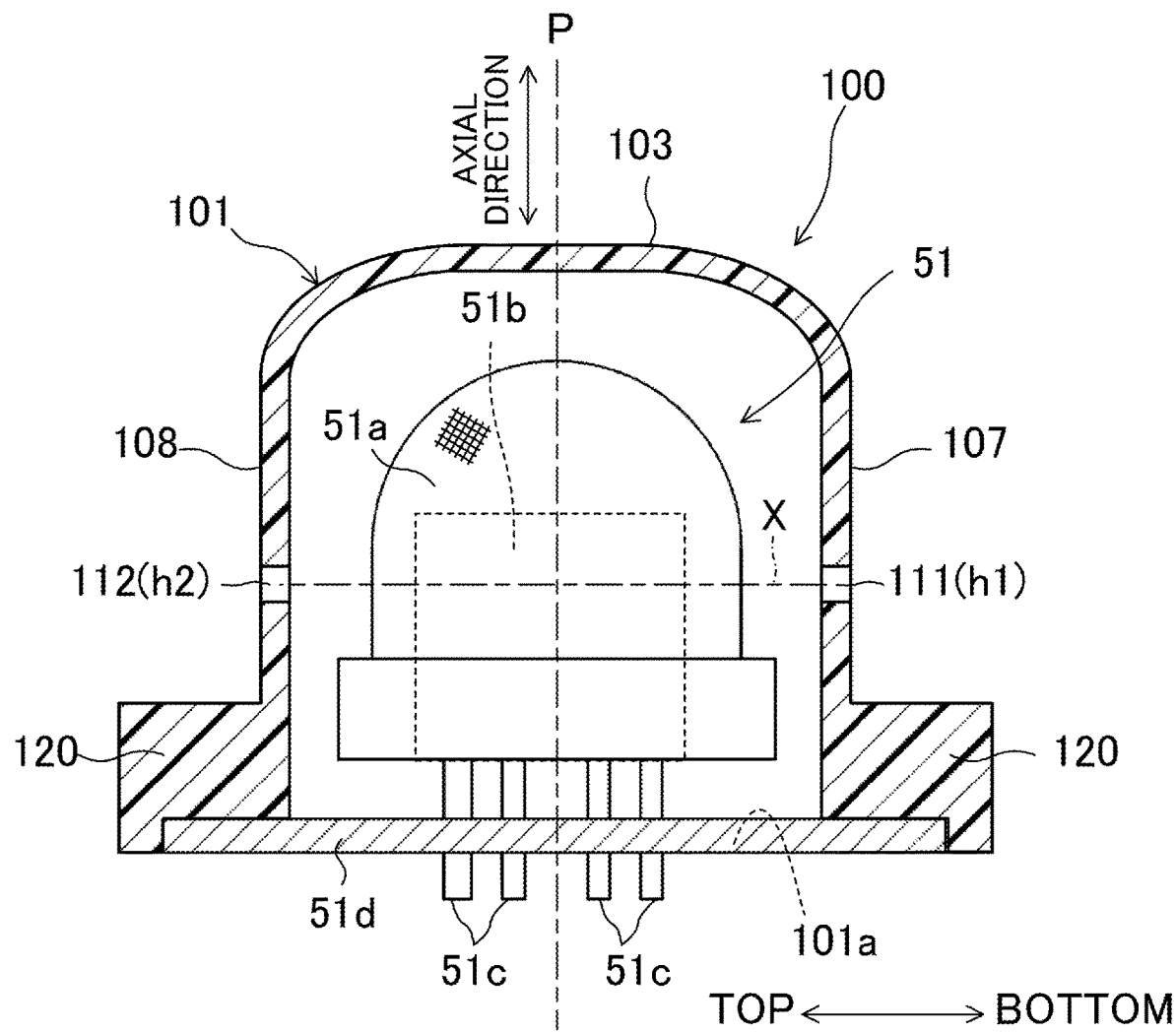
FIG. 15 is a sectional view of the cover unit.

As illustrated in FIGS. 13 to 15, the cover unit (100) has a cover (101) and a pair of attachments (120). For the sake of easy illustration, the cross section of the oxygen sensor (51) is not shown, but the appearance thereof is shown in FIG. 15. The cover (101) has a bottomed tubular shape. The cover (101) includes a tubular body (102) and a hemispherical top (103) closing one end of the body (102) in an axial direction thereof. A storage space (104) where the oxygen sensor (51) is housed is formed inside the cover (101). The pair of attachments (120) extends radially outward from portions of the cover (101) near the bottom thereof. The pair of attachments (120) faces each other with the cover (101) interposed therebetween. The attachment (120) is fastened with a fastening member such as a screw. Thus, the cover unit (100) covering the oxygen sensor (51) is fixed to the sensor casing (90) (see FIG. 12).

The cover (101) has a first flat portion (107) on the lower side, and a second flat portion (108) on the upper side. The first flat portion (107) and the second flat portion (108) are planar portions along the axial direction of the cover (101). The axial direction described herein corresponds to a direction perpendicular to an opening surface (101a) of the cover (101). The first flat portion (107) and the second flat portion (108) are formed by, for example, notches. The first flat portion (107) and the second flat portion (108) are shifted by approximately 180° about the center axis P of the cover (101). The first flat portion (107) and the second flat portion (108) each form walls facing each other. The first flat portion (107) extends from one attachment (120) to the middle of the top (103) of the cover (101). The second flat portion (108) extends from the other attachment (120) to the middle of the top of the cover (101).

An inflow path (111) is formed in the first flat portion (107). The inflow path (111) is a flow path for taking air from the sensor casing (90) into the cover (101). The inflow path (111) is formed by a first hole (h1) formed in the first flat portion (107).

An outflow path (112) is formed in the second flat portion (108). The outflow path (112) is a flow path for discharging air from the cover (101) to the outside. The outflow path (112) is formed by a second hole (h2) formed in the second flat portion (108). The inflow path (111) and the outflow path (112) face each other with the oxygen sensor (51) interposed therebetween.

The oxygen sensor (51) includes a sensor (51a) which is a main component of the oxygen sensor (51), a mesh (51b) covering the sensor (51a), a plurality of output terminals (51c) connected to the sensor (51a), and a substrate (51d) on which these output terminals (51c) are supported. The mesh (51b) protects the sensor (51a), and has a plurality of holes through which air can flow.

The sensor (51a) is arranged between the inflow path (111) and the outflow path (112) of the cover unit (100). As illustrated in FIG. 15, the sensor (51a) is positioned on a straight line X connecting the inflow path (111) and the outflow path (112) together. In other words, the sensor (51a) is positioned at a position overlapping with the inflow path (111) and the outflow path (112) in the direction of air flow through the inflow path (111) and the outflow path (112). The substrate (51d) also serves as a closing member that closes the opening surface (101a) of the cover (101). The storage space (104) is formed between the cover (101) and the substrate (51d).

<Inner Diameters of Outflow and Inflow Paths>

The inner diameter of the outflow path (112) and the inner diameter of the inflow path (111) are preferably 1 mm or more and 4 mm or less. If the inner diameter of the outflow path (112) and the inner diameter of the inflow path (111) are too small, the flow path resistance against the air flowing in the cover unit (100) is excessively great. In this case, a defect would be caused due to degradation of the responsiveness of the oxygen sensor (51).

More specifically, for example, in an operation of adjusting the oxygen concentration of the inside air (the concentration adjustment operation to be described in detail later), the oxygen concentration of the inside air is adjusted to 5%. In this case, the oxygen concentration detected by the oxygen sensor (51) is about 5%. In a case where an operation of calibrating the oxygen sensor (51) (the sensor calibration operation to be described in detail later) is performed after this operation, the outside air containing about 21% oxygen is introduced into the oxygen sensor (51). If the responsiveness of the oxygen sensor (51) is degraded, the concentration detected by the oxygen sensor (51) does not increase sufficiently responsively in the sensor calibration operation, and for this reason, a time required for calibration is prolonged (for example, 10 minutes or more). Conversely, in a case where the concentration adjustment operation is resumed after the sensor calibration operation, a degraded responsiveness of the oxygen sensor (51) results in that the concentration detected by the oxygen sensor (51) does not decrease sufficiently responsively and for this reason, the time of resumption of the concentration adjustment operation is delayed or the controllability of the oxygen concentration is degraded.

On the other hand, with the configuration in which the internal diameters of the outflow path (112) and the inflow path (111) are 1 mm or more, an excessive increase in the flow path resistance of air flowing in the cover unit (100) can be suppressed. Thus, the responsiveness of the oxygen sensor (51) can be ensured, and the above-described defect can be avoided.

with the configuration in which the internal diameters of the outflow path (112) and the inflow path (111) are 4 mm or less, an excessive increase in the flow path resistance against the air flowing in the cover unit (100) can be suppressed. Thus, passage of an excessive amount of air containing the corrosive component through the oxygen sensor (51) can be reduced. As a result, the time or frequency of contact between the oxygen sensor (51) and the corrosive component can be reduced, and deterioration of the oxygen sensor (51) can be suppressed.

In this example, the inner diameter of the outflow path (112) and the inner diameter of the inflow path (111) are 2.5 mm. The inner diameter of the outflow path (112) and the inner diameter of the inflow path (111) are preferably the same as each other, but may be different from each other by about several millimeters, for example.

<Air Current in Cover>

The oxygen sensor (51) generates heat when the oxygen sensor (51) and the oxygen sensor (51) is turned ON with electricity supply thereto. More specifically, the oxygen sensor (51) is the zirconia sensor, and would generate heat up to about 450° C. when the oxygen sensor (51) is turned ON with electricity supply thereto. Thus, in operation of the oxygen sensor (51), an ascending air current can be formed in the storage space (104) in the cover (101). As a result, part of air in the sensor casing (90) can be easily introduced into the cover (101).

Particularly, since the outflow path (112) is positioned at the upper portion of the cover (101), the ascending air current due to heat generation is easily guided to the outflow path (112). Accordingly, an air flow can be easily formed inside the cover (101), and the heat of the oxygen sensor (51) can be quickly released to the outside.

<Controller>

The controller (55) controls the concentration adjustment operation in which the oxygen concentration and the carbon dioxide concentration of air in the container body (2) are adjusted to desired concentrations. More specifically, the controller (55) controls operation of the gas supply unit (30), the exhauster (46), and the sensor unit (50) based on measurement results obtained from the oxygen sensor (51) and the carbon dioxide sensor (52) such that the composition (the oxygen concentration and the carbon dioxide concentration) of the air in the container body (2) is controlled to a desired composition (e.g., 5% oxygen and 5% carbon dioxide).

The controller (55) includes, for example, a microcomputer that controls various components of the CA system (60) and a storage medium, such as a memory or a disk, that stores executable control programs. Detailed structure and algorithm of the controller (55) may be any combination of hardware and software.

—Operation—

<Operation of Refrigerant Circuit>

In this embodiment, a unit controller (150) illustrated in FIG. 3 performs a cooling operation of cooling air in the container body (2).

In the cooling operation, the unit controller (150) controls operation of the compressor (21), the expansion valve (23), the external fan (25), and the internal fans (26) such that the temperature of the inside air reaches a desired target temperature based on measurement results obtained by a not-shown temperature sensor. Refrigerant circulates in the refrigerant circuit (20) to perform a vapor compression refrigeration cycle. The inside air guided from the container body (2) to the internal storage space (S2) by the internal fans (26) is cooled by the refrigerant flowing in the evaporator (24) when passing through the evaporator (24). The inside air cooled by the evaporator (24) passes through the underfloor flow path (19a), and is blown again into the container body (2) through the blow-out port (18b). Thus, the air in the container body (2) is cooled.

<Operation of Gas Supply Unit>

(Gas Generation Operation) The gas supply unit (30) alternately repeats, at a predetermined time interval, a first operation (see FIG. 4) in which the first adsorption column (34) is pressurized while the second adsorption column (35) is depressurized and a second operation (see FIG. 5) in which the first adsorption column (34) is depressurized while the second adsorption column (35) is pressurized, thereby generating nitrogen-enriched air and oxygen-enriched air. The controller (55) switch over these operations by operating the first and second directional control valves (32, 33).

<<First Operation>>

In the first operation, the controller (55) switches both the first and second directional control valves (32, 33) to the first state illustrated in FIG. 4. Thus, the air circuit (3) is brought into the first connection state in which the first adsorption column (34) communicates with the discharge port of the first pump mechanism (31a) and is blocked from the suction port of the second pump mechanism (31b) and the second adsorption column (35) communicates with the suction port of the second pump mechanism (31b) and is blocked from the discharge port of the first pump mechanism (31a). In this first connection state, the outside air compressed by the first pump mechanism (31a) is supplied to the first adsorption column (34), while the second pump mechanism (31b) sucks, from the second adsorption column (35), the nitrogen-enriched air having a higher nitrogen concentration and a lower oxygen concentration than those of the outside air.

More specifically, the first pump mechanism (31a) sucks the outside air through the outside air passage (41), compresses the outside air, and discharges the compressed outside air (compressed air) to the compression passage (42). The compressed air discharged to the compression passage (42) flows in the compression passage (42). Then, the compressed air is supplied to the first adsorption column (34) through the compression passage (42).

In this manner, the compressed air flows into the first adsorption column (34), and the nitrogen component contained in the compressed air adsorbs to the adsorbent. During the first operation, the first pump mechanism (31a) supplies the compressed outside air to the first adsorption column (34), and the nitrogen component in the outside air adsorbs to the adsorbent. As a result, the oxygen-enriched air having a lower nitrogen concentration and a higher oxygen concentration than those of the outside air is generated. The oxygen-enriched air flows from the first adsorption column (34) to the oxygen discharge passage (45).

The second pump mechanism (31b) sucks the air from the second adsorption column (35). In the sucking, the second pump mechanism (31b) also sucks the nitrogen component adsorbed on the adsorbent in the second adsorption column (35) together with the air, thereby desorbing the nitrogen component from the adsorbent. In this manner, during the first operation, the air in the second adsorption column (35) is sucked by the second pump mechanism (31b), and the nitrogen component adsorbed on the adsorbent desorbs from the adsorbent. Accordingly, the nitrogen-enriched air containing the nitrogen component desorbed from the adsorbent and having a higher nitrogen concentration and a lower oxygen concentration than those of the outside air is generated. The nitrogen-enriched air is sucked into the second pump mechanism (31b), compressed, and discharged to the supply passage (44).

<<Second Operation>>

In the second operation, the controller (55) switches both the first and second directional control valves (32, 33) to the second state illustrated in FIG. 5. Thus, the air circuit (3) is brought into the second connection state in which the first adsorption column (34) communicates with the suction port of the second pump mechanism (31b) and is blocked from the discharge port of the first pump mechanism (31a) and the second adsorption column (35) communicates with the discharge port of the first pump mechanism (31a) and is blocked from the suction port of the second pump mechanism (31b). In this second connection state, the outside air compressed by the first pump mechanism (31a) is supplied to the second adsorption column (35), while the second pump mechanism (31b) sucks the nitrogen-enriched air from the first adsorption column (34).

More specifically, the first pump mechanism (31a) sucks the outside air through the outside air passage (41), compresses the outside air, and discharges the compressed outside air (compressed air) to the compression passage (42). The compressed air discharged to the compression passage (42) flows in the compression passage (42). Then, the compressed air is supplied to the second adsorption column (35) through the compression passage (42).

In this manner, the compressed air flows into the second adsorption column (35), and the nitrogen component contained in the compressed air adsorbs to the adsorbent. During the second operation, the first pump mechanism (31a) supplies the compressed outside air to the second adsorption column (35), and the nitrogen component in the outside air adsorbs to the adsorbent. As a result, the oxygen-enriched air having a lower nitrogen concentration and a higher oxygen concentration than those of the outside air is generated. The oxygen-enriched air flows out from the second adsorption column (35) to the oxygen discharge passage (45).

The second pump mechanism (31b) sucks the air from the first adsorption column (34). In the sucking, the second pump mechanism (31b) sucks the nitrogen component adsorbed on the adsorbent in the first adsorption column (34) together with the air, thereby desorbing the nitrogen component from the adsorbent. In this manner, during the second operation, the air in the first adsorption column (34) is sucked by the second pump mechanism (31b), and the nitrogen component on the adsorbent desorbs from the adsorbent. Accordingly, the nitrogen-enriched air containing the nitrogen component desorbed from the adsorbent and having a higher nitrogen concentration and a lower oxygen concentration than those of the outside air is generated. The nitrogen-enriched air is sucked into the second pump mechanism (31b), compressed, and discharged to the supply passage (44).

(Gas Supply Operation/Gas Discharge Operation)

The supply-discharge switching mechanism (70) switches the gas supply unit (30) between the gas supply operation in which the nitrogen-enriched air generated in the air circuit (3) is supplied into the container body (2) and the gas discharge operation in which the generated nitrogen-enriched air is not supplied into, but discharged to the outside of, the container body (2) for a predetermined time from the start of the desorption operation.

In the gas supply operation, the controller (55) controls the exhaust on-off valve (72) to the closed state and controls the supply on-off valve (73) to the open state, as illustrated in FIGS. 4 and 5. As a result, the nitrogen-enriched air generated alternately in the first and second adsorption columns (34, 35) is supplied into the container body (2) through the supply passage (44), and the oxygen-enriched air is discharged to the outside through the oxygen discharge passage (45).

Although not shown in the figure, in the gas discharge operation, the controller (55) controls the exhaust on-off valve (72) to the open state, and controls the supply on-off valve (73) to the closed state. As a result, the nitrogen-enriched air generated alternately in the first and second adsorption columns (34, 35) and discharged to the supply passage (44) flows from the exhaust connection passage (71) into the oxygen discharge passage (45), and is then discharged to the outside together with the oxygen-enriched air flowing in the oxygen discharge passage (45).

(Outside Air Introduction Operation)

In this embodiment, an outside air introduction operation of introducing the outside air into the container body (2) can also be performed. In the outside air introduction operation illustrated in FIG. 6, the first directional control valve (32) is set to the first state, the second directional control valve (33) is set to the second state, and the bypass on-off valve (48) is opened. The supply on-off valve (73) is opened, and the branch on-off valve (82) is closed. When the air pump (31) is started in this state, the outside air flows in the outside air introduction passage (40) formed by the outside air passage (41), part of the compression passage (42), the bypass passage (47), and part of the supply passage (44) as indicated by a thick solid line. This is because the passage resistance of the outside air introduction passage (40) is less than the passage resistance of the passage through the directional switch valves (32, 33) and the adsorption columns (34, 35). Then, the air having the same composition as that of the outside air flowing in the outside air introduction passage (40) is pushed into the container body (2).

<Concentration Adjustment Operation of CA System>

In this embodiment, the CA system (60) performs, by the controller (55), the concentration adjustment operation in which the composition (the oxygen concentration and the carbon dioxide concentration) of the air in the container body (2) is adjusted to a desired composition (e.g., 5% oxygen and 5% carbon dioxide). In the concentration adjustment operation, operation of the gas supply unit (30) and the exhauster (46) is controlled based on the measurement results obtained by the oxygen sensor (51) and the carbon dioxide sensor (52) such that the composition of the air in the container body (2) is adjusted to a desired composition.

During the concentration adjustment operation, the controller (55) controls the branch on-off valve (82) to the closed state. During the concentration adjustment operation, the controller (55) communicates with the unit controller (150), and the unit controller (150) rotates the internal fans (26). As a result, the oxygen sensor (51) and the carbon dioxide sensor (52), supplied with the inside air by the internal fans (26), measure the oxygen concentration and the carbon dioxide concentration of the inside air, respectively.

During the concentration adjustment operation, the gas supply operation is performed by alternately repeating the first operation and the second operation, thereby adjusting the oxygen concentration in the container. At this time, the exhaust valve (46b) of the exhauster (46) is controlled to the open state, and the inside air as much as the nitrogen-enriched air supplied into the container body (2) by the gas supply operation is discharged. When the oxygen concentration of the inside air decreases to a predetermined value (e.g., 8%), the controller (55) stops operation of the gas supply unit (30) to stop the gas supply operation, and closes the exhaust valve (46b) to stop the exhaust operation. Since the plants (15) breathe in the container body (2), the oxygen concentration of the air in the container body (2) decreases and eventually reaches a target oxygen concentration of 5%.

An operation of increasing the oxygen concentration in the inside air can be performed by the outside air introduction operation in which the bypass on-off valve (48) is opened and the outside air sucked into the air pump (31) is supplied into the container body (2) by bypassing the first and second adsorption columns (34, 35). At this time, since the outside air passes through the cooling portion (40a), an increase in the temperature of the inside air is suppressed.

Although details are omitted, the oxygen concentration (and the carbon dioxide concentration) of the inside air can also be adjusted in such a manner that the gas supply operation, the gas discharge operation, and the outside air introduction operation are switched as necessary.

(Supply Air Measurement Operation)

In this embodiment, the supply air measurement operation in which the oxygen concentration of the nitrogen-enriched air generated in the gas supply unit (30) is measured is performed by a user's instruction or periodically (e.g., every 10 days). The supply air measurement operation is performed upon the stop of the internal fans (26) during the concentration adjustment operation or the gas supply operation such as a test operation.

During the gas supply operation, the controller (55) controls the branch on-off valve (82) to the open state, and controls the supply on-off valve (73) to the closed state. Accordingly, the nitrogen-enriched air flowing in the supply passage (44) entirely flows into the branch piping (81). The nitrogen-enriched air having flowed into the branch piping (81) is introduced into the oxygen sensor (51), and the oxygen concentration thereof is measured.

In this manner, the oxygen concentration of the nitrogen-enriched air generated in the gas supply unit (30) is measured so that it can be checked whether or not the composition (the oxygen concentration and the nitrogen concentration) of the nitrogen-enriched air generated in the gas supply unit (30) is in a desired state.

(Sensor Calibration Operation)

Figure 7:
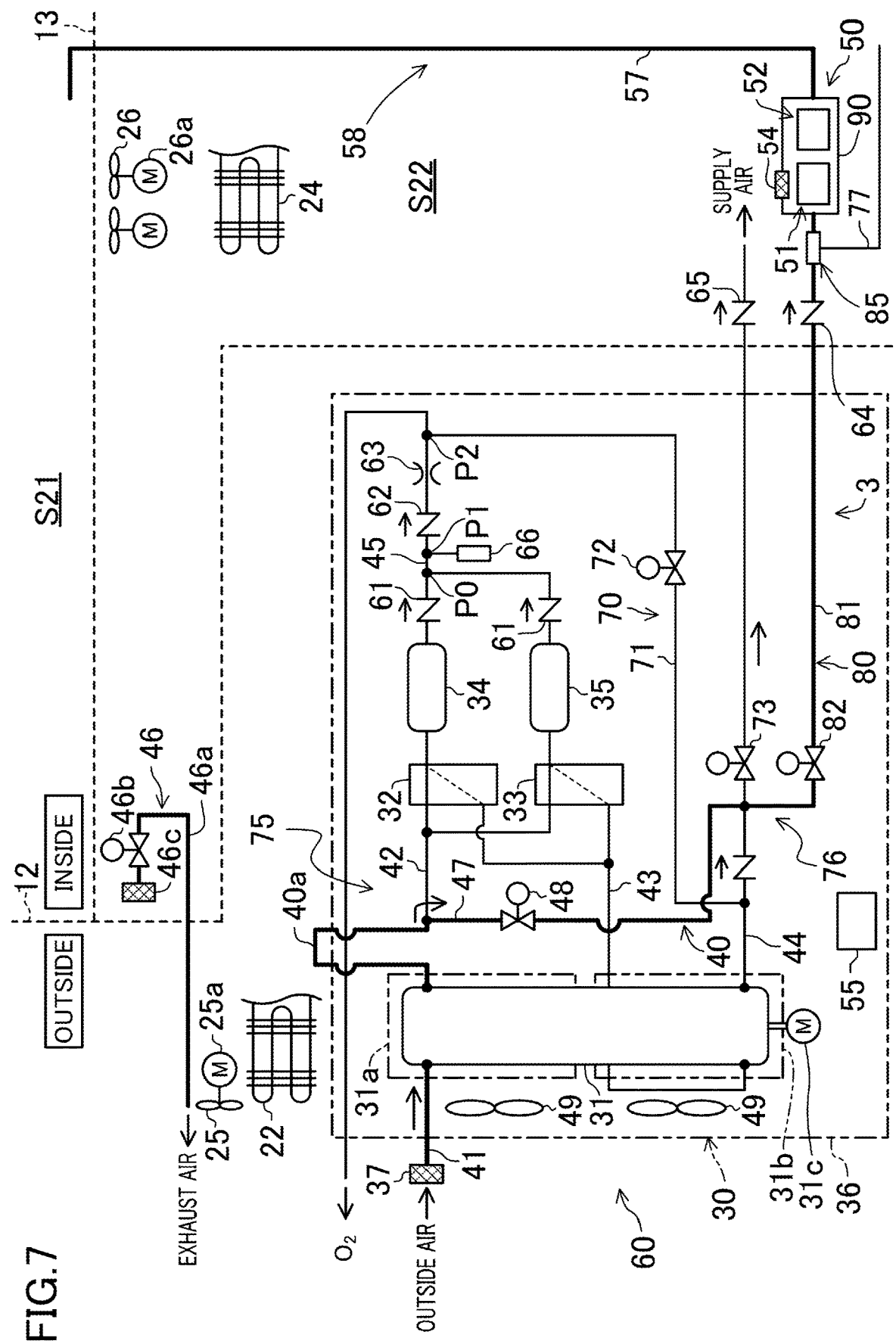
FIG. 7 is a piping system diagram illustrating the air circuit of the CA system of the transportation refrigeration apparatus of FIG. 1, which illustrates the flow of air in a sensor calibration operation.

In this embodiment, the sensor calibration operation of FIG. 7 in which the oxygen sensor (51) is calibrated through introduction of the outside air into the sensor unit (50) can be performed. The sensor calibration operation can be performed in a short time (about 10 minutes) by temporarily stopping concentration adjustment during cooling of the inside of the container, and then, operation can return to the concentration adjustment operation, for example.

In the sensor calibration operation, the first directional control valve (32) is set to the first state, the second directional control valve (33) is set to the second state, and the bypass on-off valve (48) is opened. The supply on-off valve (73) is closed, and the branch on-off valve (82) is opened. When the air pump (31) is started in this state, the outside air flows in the first passage (75) and the second passage (76) and is introduced into the sensor unit (50). The oxygen sensor (51) is calibrated such that the detection value indicates the oxygen concentration of the outside air.

During the sensor calibration operation, the outside air passes through the gas-liquid separator (85). Thus, the outside air from which at least part of moisture has been removed comes into contact with the oxygen sensor (51).

(Air Flow in Sensor Casing)

In a normal operation, the inside air flows into the sensor casing (90) through the second introduction port (94b) in FIG. 10. The inside air having flowed in through the second introduction port (94b) flows toward the ejection port (95) while filling the inside of the sensor casing (90) (see a path (R1)). At this time, the body (102) of the cover (101) is positioned between the second introduction port (94b) and the oxygen sensor (51). In addition, since the oxygen sensor (51) is covered with the cover (101), contact between the corrosive component and the oxygen sensor (51) is reduced even if the inside air contains the corrosive component.

In the supply air measurement operation or the sensor calibration operation, the outside air in the container flows into the sensor casing (90) through the first introduction port (94a) in FIG. 10. The air is air whose composition has been adjusted by the adsorption columns (34, 35) in the supply air measurement operation, and is outside air which has bypassed the adsorption columns (34, 35) in the sensor calibration operation. The air flows toward the ejection port (95) while filling the inside of the sensor casing (90) (see a path (R2)). In this case as well, the body (102) of the cover (101) is positioned between the second introduction port (94b) and the oxygen sensor (51). In addition, since the oxygen sensor (51) is covered with the cover (101), contact between the corrosive component and the oxygen sensor (51) is reduced even if the outside air in the container contains the corrosive component.

Advantages of First Embodiment

In the first embodiment, the cover (101) that covers around the oxygen sensor (51) is provided. Thus, the cover (101) can reduce contact of the corrosive component in air with the oxygen sensor (51). As a result, deterioration of the oxygen sensor (51) can be suppressed.

With the configuration in which the inner diameter of the inflow path (111) and the inner diameter of the outflow path (112) in the cover unit (100) are 1 mm or more, the flow path resistance in the cover (101) can be reduced and a decline in the responsiveness of the oxygen sensor (51) can be suppressed. Accordingly, the time of the sensor calibration operation can be shortened, and transition from the sensor calibration operation to the concentration adjustment operation can be quickly made, for example.

By setting the inner diameter of the inflow path (111) and the inner diameter of the outflow path (112) in the cover unit (100) to 4 mm or less, the time and frequency of contact between the oxygen sensor (51) and the corrosive component can be reduced. As a result, deterioration of the oxygen sensor (51) can be suppressed, and the durable life of the oxygen sensor (51) can be extended.

The outflow path (112) is positioned at the upper portion of the cover (101). Thus, the heat of the oxygen sensor (51) can be discharged to the outside of the cover (101), so that an excessive increase in the temperature of air inside the cover (101) can be suppressed. Such relatively-high temperature air is cooled upon the stop of the oxygen sensor (51) so that generation of dew condensation water inside the cover (101) can be reduced. In addition, the discharging the air from the upper side of the cover (101) can encourage the ascending air current caused due to heat generation of the oxygen sensor (51).

The inflow path (111) is positioned at the lower portion of the cover (101). Thus, water inside the cover (101) can be discharged to the outside of the cover (101) by the own weight of the water through the inflow path (111).

The sensor (51a) of the oxygen sensor (51) is positioned between the inflow path (111) and the outflow path (112). Thus, air easily passes around the sensor (51a) so that the responsiveness of the oxygen sensor (51) can be improved.

The inflow path (111) is formed by the first hole (h1) formed at the cover (101), and the outflow path (112) is formed by the second hole (h2) formed at the cover (101). Since the inflow path (111) and the outflow path (112) are formed by the holes (h1, h2) as described above, the flow path lengths of the inflow path (111) and the outflow path (112) are shortened. Thus, while the inner diameters of the inflow path (111) and the outflow path (112) are secured to some extent, the flow path resistances thereof can be reduced. The inflow path (111) and the outflow path (112) are also easily prepared.

The oxygen sensor (51) is configured to generate heat while being turned ON, and the cover (101) is configured to generate the air flow due to the heat generation of the oxygen sensor (51). Thus, the air flow can also be ensured in the cover (101), and the oxygen concentration can be accurately detected by the oxygen sensor (51).

The sensor casing (90) includes the introduction port (94) for introducing air into the sensor casing (90), and the cover (101) is arranged between the introduction port (94) and the oxygen sensor (51). Thus, contact of the corrosive component having entered through the introduction port (94) with the oxygen sensor (51) can be reduced.

The introduction port (94) is arranged below the oxygen sensor (51), and the cover (101) has the portion (the body (102)) arranged below the oxygen sensor (51). Thus, contact of the corrosive component having entered through the introduction port (94) below the oxygen sensor (51) with the oxygen sensor (51) can be reduced.

The introduction port (94) includes the first introduction port (94a) for introducing air from the target space into the sensor casing (90) and the second introduction port (94b) for introducing air outside the target space into the sensor casing (90), at least one of the first introduction port (94a) or the second introduction port (94b) is arranged below the oxygen sensor (51), and the cover (101) has the portion arranged below the oxygen sensor (51).

Thus, contact of the corrosive component having entered through the first introduction port (94a) or the second introduction port (94b) below the oxygen sensor (51) with the oxygen sensor (51) can be reduced.

In the first embodiment, at least part of moisture in air flowing into the sensor casing (90) from the branch piping (81) is removed by the gas-liquid separator (85). Thus, failure of the oxygen sensor (51) or the carbon dioxide sensor (52) due to adhesion of the moisture can be reduced.

Variations of First Embodiment

First Variation

In the first embodiment, both the first introduction port (94a) and the second introduction port (94b) are arranged below the oxygen sensor (51), but either the first introduction port (94a) or the second introduction port (94b) may be arranged below the oxygen sensor (51).

In a case where the first introduction port (94a) is arranged below the oxygen sensor (51) and part of the cover (101) is arranged therebetween, contact between the oxygen sensor (51) and the corrosive component due to the outside air in sensor calibration can be reduced. In a case where the second introduction port (94b) is arranged below the oxygen sensor and part of the cover (101) is arranged therebetween, contact between the oxygen sensor (51) and the corrosive component due to the inside air in the normal operation can be reduced.

Second Variation

In the cover unit (100) of the first embodiment, the holes (h1, h2) at the cover (101) form the inflow path (111) and the outflow path (112). However, tubular portions (131, 132) of the cover (101) may be provided at the cover unit (100) to form the inflow path (111) and the outflow path (112).

Figure 16:
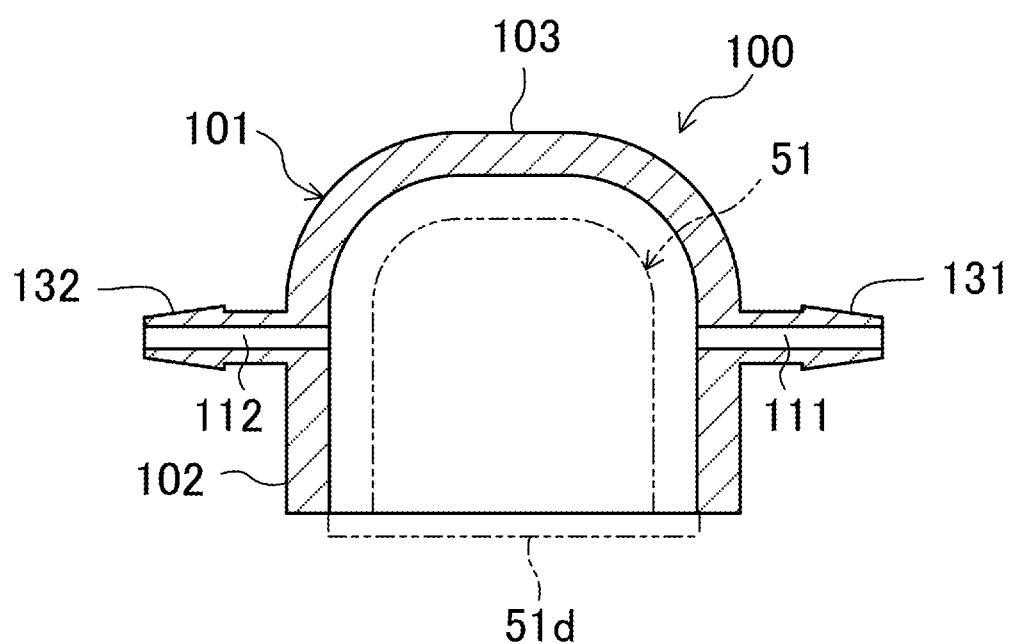
FIG. 16 is a sectional view of a cover unit according to a second variation of the first embodiment.

As illustrated in FIG. 16, in the cover unit (100) of the second variation, the first tubular portion (131) and the second tubular portion (132) are connected to around the body (102) of the cover (101). The inflow path (111) is formed inside the first tubular portion (131). The inflow path (111) communicates with the outside of the cover (101) and the storage space (104). The outflow path (112) is formed inside the second tubular portion (132). The outflow path (112) communicates with the outside of the cover (101) and the storage space (104). In this example, the first tubular portion (131) and the second tubular portion (132) face each other. Other basic configurations are the same as those of the first embodiment.

Second Embodiment

A second embodiment is an example where in addition to the cover unit (100) of the first embodiment, an adsorbing member (105) for adsorbing a corrosive component in air is employed as a contact reducer.

Figure 17:
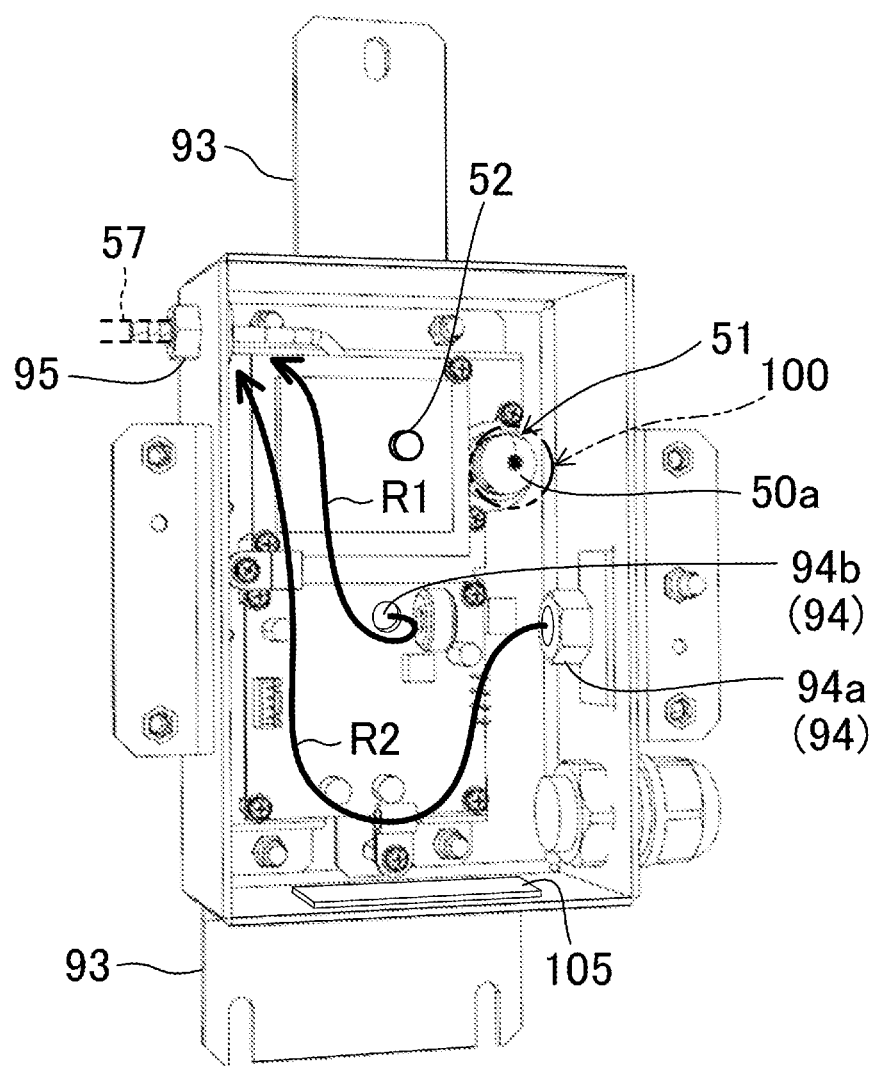
FIG. 17 is a perspective view illustrating the inside of a sensor casing according to a second embodiment.

The adsorbing member (105) may be arranged inside a sensor casing (90). FIG. 17 illustrates an example where the adsorbing member (105) is provided on the bottom of the sensor casing (90). The adsorbing member (105) includes a base substrate and an adsorbent (for example, zeolite or active carbon) supported on the base material.

The second embodiment has, including the air circuit (3), the same configuration as that of the first embodiment, except that the adsorbing member (105) is provided instead of the wall member (101). Thus, description of other configurations of the adsorbing member (105) will be omitted.

In the second embodiment, the corrosive component contained in air introduced into the sensor casing (90) adsorbs to the adsorbing member (105) in the sensor casing (90). Thus, contact of the corrosive component with an oxygen sensor (51) can be reduced.

The adsorbing member (105) may be provided inside the sensor casing (90) together with the wall member (101) of the first embodiment. According to this configuration, contact of the corrosive component with the oxygen sensor (51) can be reduced by both the wall member (101) and the adsorbing member (105).

Variations of Second Embodiment

First Variation

Figure 18:
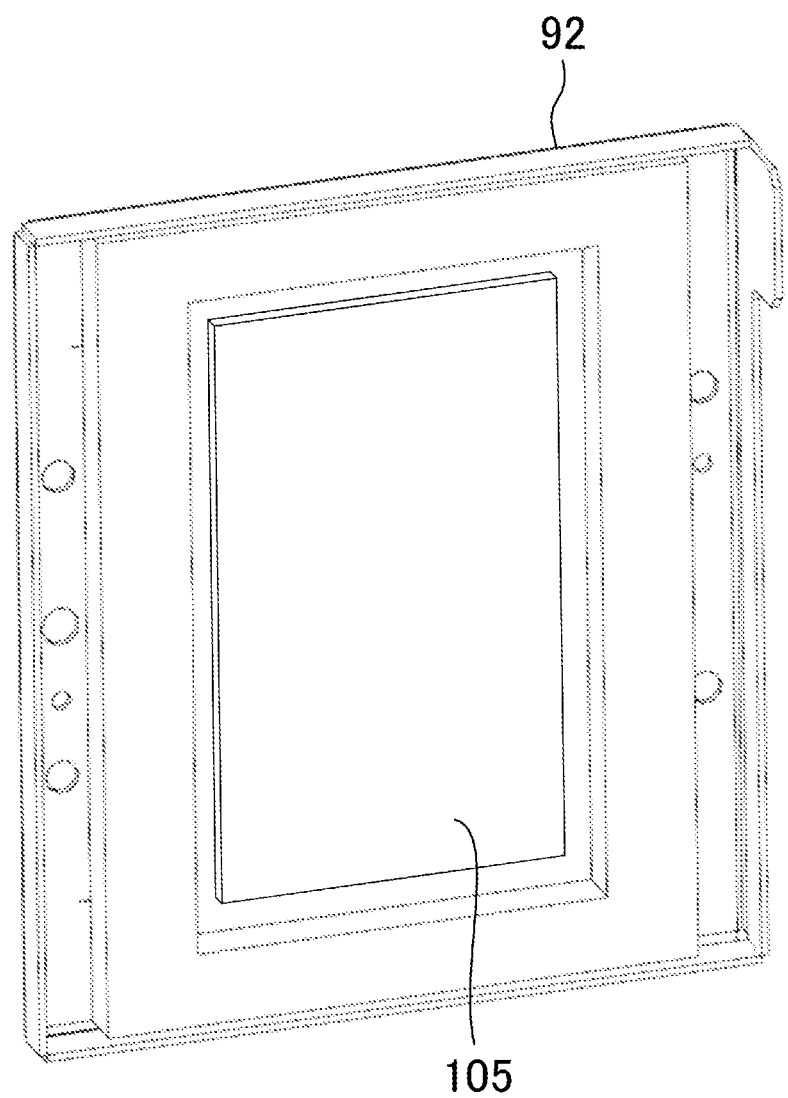
FIG. 18 is a perspective view of a configuration in which an adsorbing member is provided on a case cover according to a first variation of the second embodiment.

The adsorbing member (105) may be arranged at a position, such as a rear surface of a case cover (92) of the sensor casing (90) as illustrated in FIG. 18, thereby being different from the illustration of FIG. 17 where the adsorbing member (105) is inside the sensor casing (90). According to such a configuration, contact of the corrosive component with the oxygen sensor (51) can be reduced by adsorption of the corrosive component in the air to the adsorbing member (105).

Second Variation

The adsorbing member (105) may be provided in the air circuit (3) in arrangement different from those of the examples of FIGS. 17 and 18.

Figure 19:
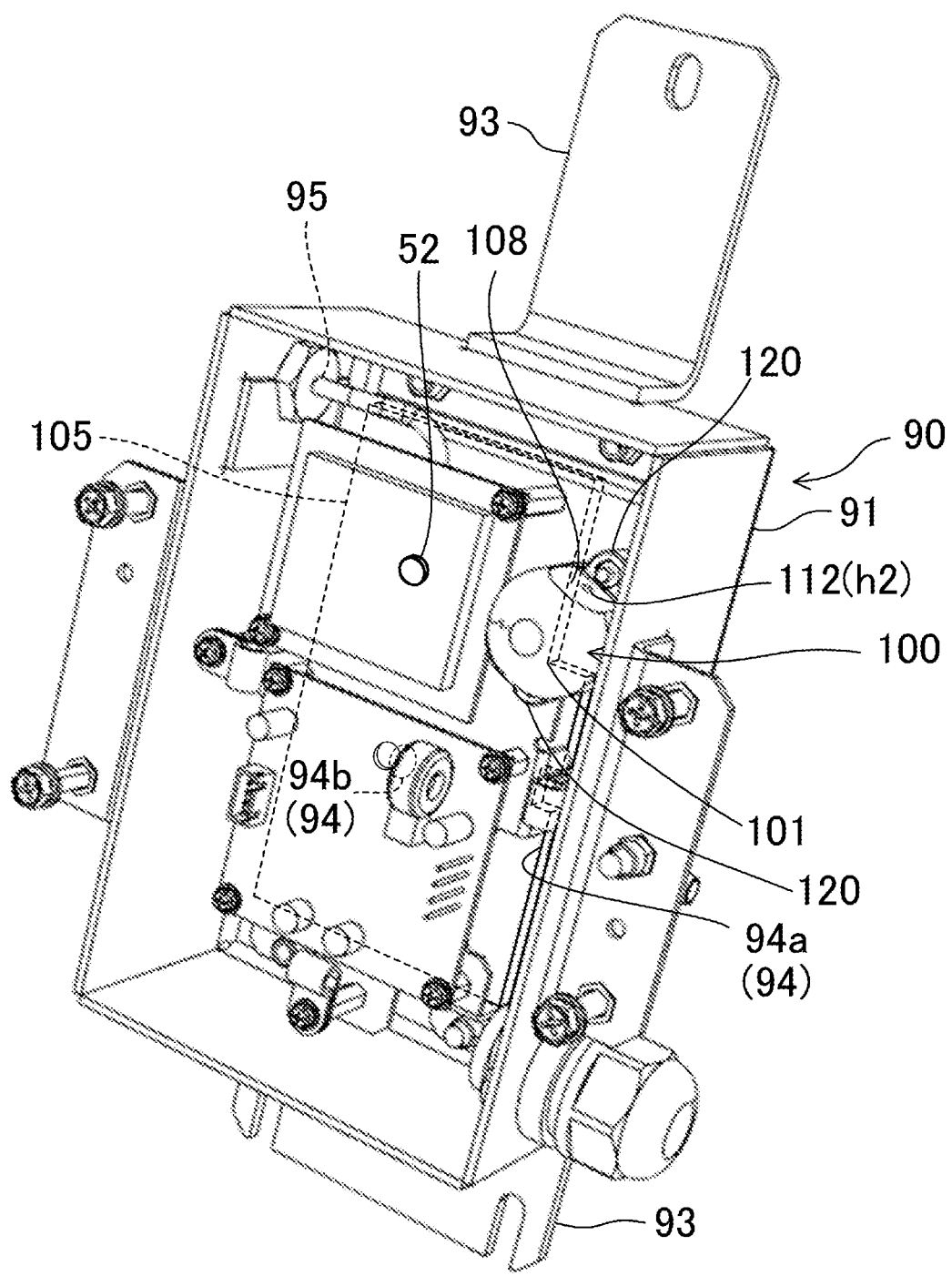
FIG. 19 is a perspective view illustrating the inside of a sensor casing according to a second variation of the second embodiment.

As illustrated in FIG. 19, the adsorbing member (105) is arranged on a rear surface (a surface at which a second introduction port (94b) is formed) side of the sensor casing (90), and is positioned at the same surface as that of the oxygen sensor (51) and the cover (101). The adsorbing member (105) includes a substantially-rectangular base material on which an adsorbent is supported.

In this configuration, if air passing through the second introduction port (94b) contains the corrosive component, the corrosive component effectively adsorbs to the adsorbing member (105). The air further passes through an inflow path (111) of the cover (101), and is introduced into the cover (101). Thus, contact of the corrosive component with the oxygen sensor (51) can be effectively reduced.

Third Variation

Figure 20:
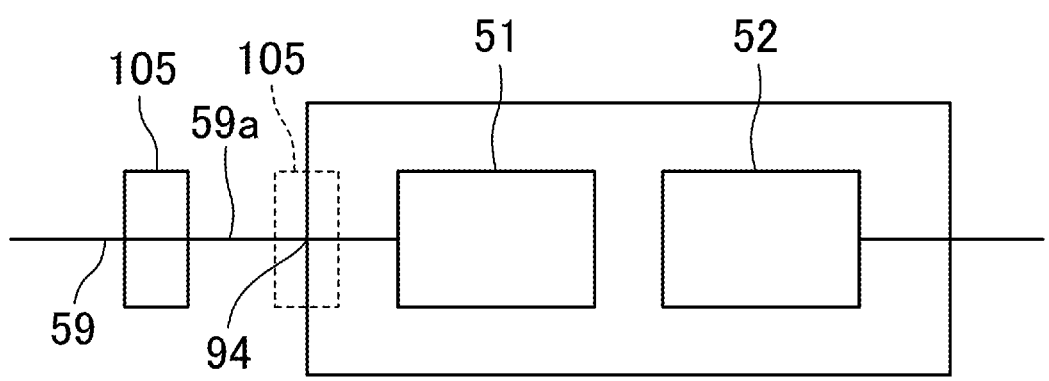
FIG. 20 is a partially-enlarged diagram of an air circuit of a CA system according to a third variation of the second embodiment.

FIG. 20 is a partially-enlarged view of the air circuit (3) according to a third variation. In this third variation, the adsorbing member (105) is arranged in a connection piping (59) which is a first introduction path (59a) for introducing air into the sensor casing (90), as shown in the figure. The adsorbing member (105) may be arranged, for example, together with a membrane filter (54) in an introduction port (94) at which the connection piping (59) is connected to the sensor casing (90), as indicated by the virtual line in FIG. 20.

A plurality of adsorbing members (105) provided in the air circuit (3) may be provided, so that the plurality of adsorbing members (105) be arranged inside the sensor casing (90) and at the other position other than the sensor casing (90). Optionally, the plurality of adsorbing members (105) may be arranged both in the connection piping (59) which is the first introduction path (59a) for introducing the outside air into the sensor casing (90) and at a second introduction port (94b) which forms a second introduction path (59b) for introducing the inside air into the sensor casing (90).

According to the third variation, the corrosive component in air introduced into the sensor casing (90) adsorbs to the adsorbing member (105) in the vicinity of the sensor casing (90). As a result, contact of the corrosive component with the oxygen sensor (51) is reduced, and deterioration of the oxygen sensor (51) is suppressed.

Fourth Variation

The adsorbing member (105) may be provided at a position other than that inside the sensor casing (90).

Figure 21:
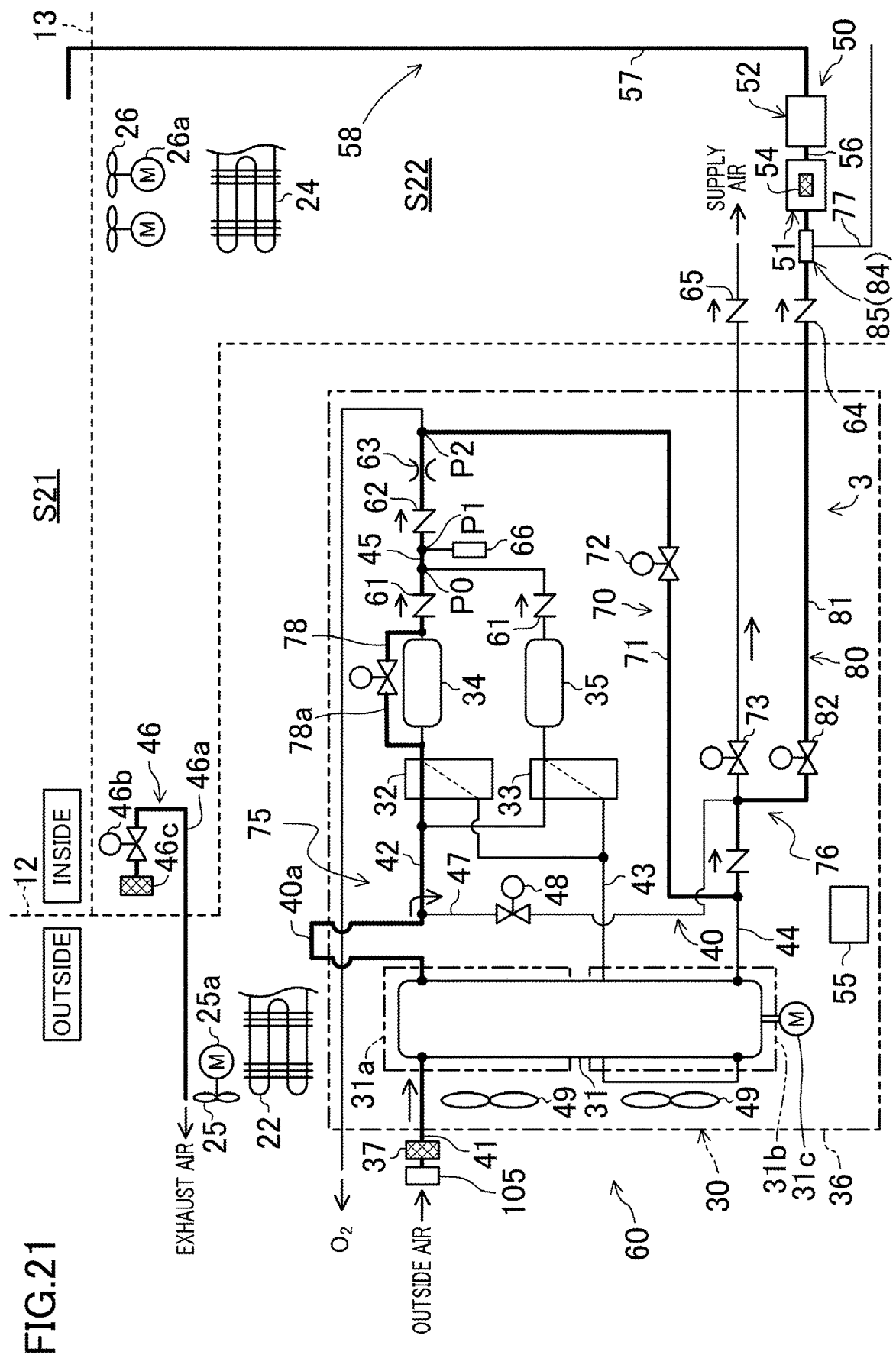
FIG. 21 is a partially-enlarged diagram of an air circuit of a CA system according to a fourth variation of the second embodiment.

FIG. 21 is a diagram illustrating the air circuit (3) of the CA system according to a fourth variation of the second embodiment. In this fourth variation, the adsorbing member (105) is arranged together with the membrane filter (76) in an inflow portion through which the outside air flows into the air circuit (3).

In the fourth variation, one end of the bypass passage (78) arranged in parallel with the first adsorption column (34) is connected to the compression passage (42), and the other end is connected to the oxygen discharge passage (45). The bypass on-off valve (78a) is provided in the bypass passage (78). In this configuration, the outside air flowing in the bypass passage (78) having the bypass on-off valve (78a), the oxygen discharge passage (45), the exhaust connection passage (71), the supply passage (44), and the branch piping (81) in this order can be introduced into the oxygen sensor (51) in calibration. In this manner, the second passage (76) may be a passage which is branched from the first passage (75) and then merges as long as it is a passage which is branched from the first passage and through which the outside air can be introduced into the oxygen sensor (51).

The other configurations of the fourth variation are the same as those of the first variation.

According to the fourth variation, the corrosive component contained in the outside air flowing in the air circuit (3) can adsorb to the adsorbing member (105). Thus, contact of the corrosive component with the oxygen sensor (51) can be reduced in a calibration operation of introducing the outside air into the oxygen sensor (51).

Third Embodiment

Figure 22:
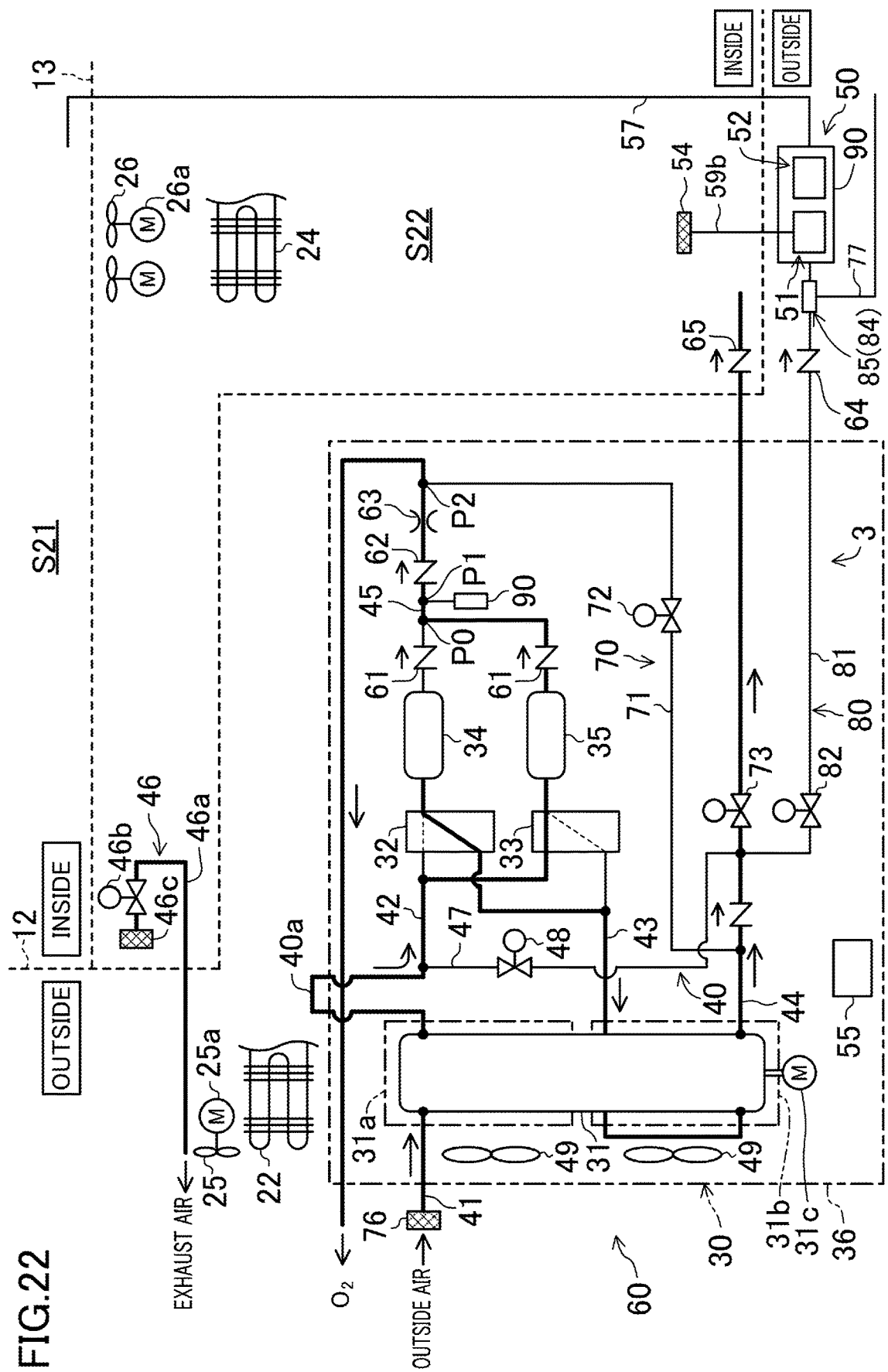
FIG. 22 is a piping system diagram illustrating an air circuit of a CA system according to a third embodiment.
Figure 23:
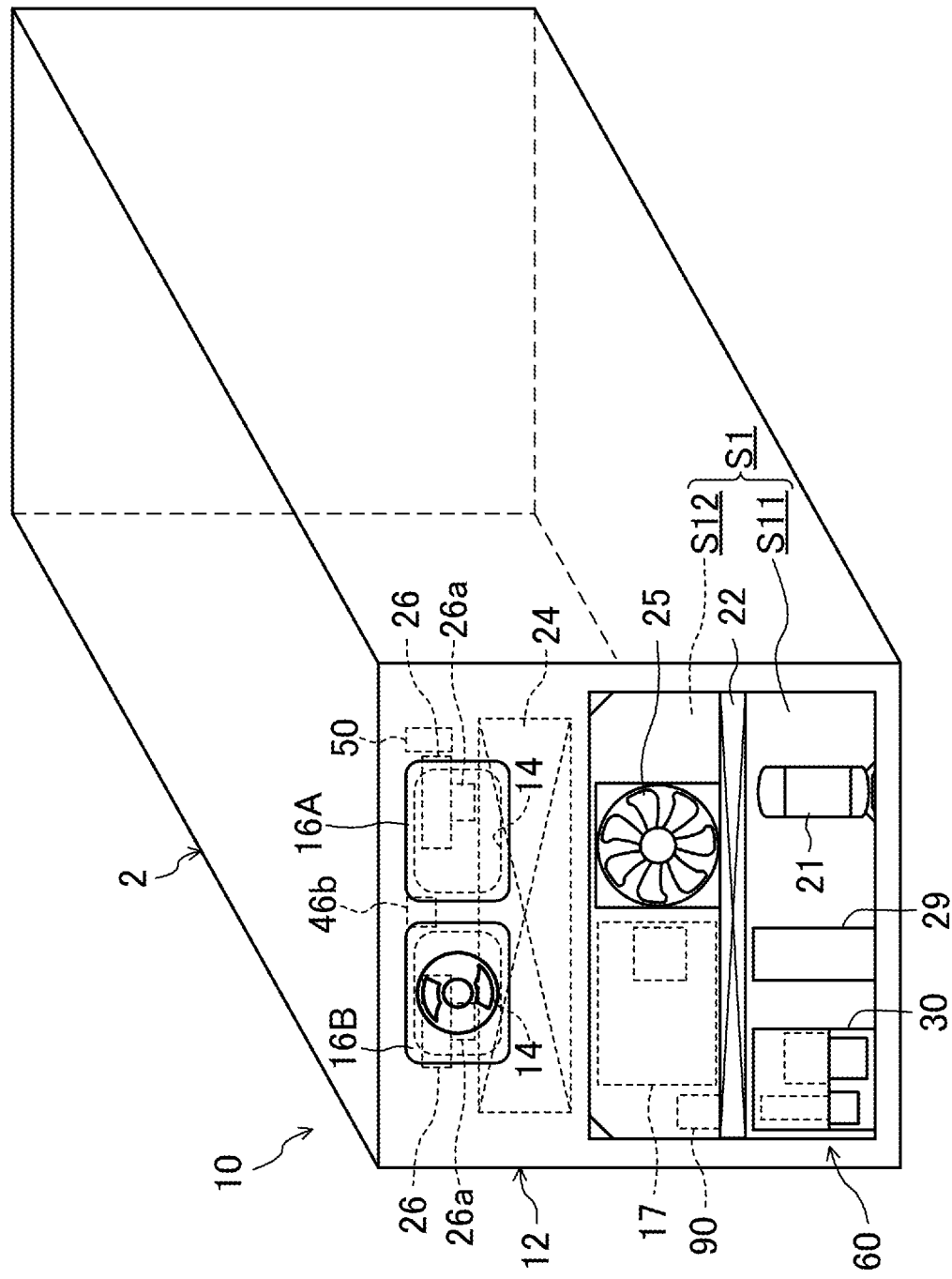
FIG. 23 is a perspective view of a transportation refrigeration apparatus according to the third embodiment.

As illustrated in FIGS. 22 and 23, a sensor casing (90) may be arranged not in an internal space but in an external space. As illustrated in a piping system diagram of FIG. 22, the sensor casing (90) arranged outside a container is connected through a second introduction path (59b) to a membrane filter (54) arranged in a secondary space (S22) inside the container. According to such a configuration, contact of a corrosive component in air with an oxygen sensor (51) can also be reduced.

In the configuration in which the sensor casing (90) is arranged in the external space as described above, the first introduction port (94a) illustrated in FIGS. 9 to 11 introduces outside air into the sensor casing (90) in calibration of the oxygen sensor (51), and the second introduction port (94b) introduces inside air into the sensor casing (90).

Other Embodiments

The above-described embodiments may be modified as follows.

For example, in the above-described embodiments, the oxygen sensor (51) has been described as the gas sensor to be avoided from being deteriorated due to the corrosive component. However, such deterioration is assumed to be caused in a gas sensor other than the oxygen sensor (51). Thus, the cover (101) and the contact reducer (105) of the above-described embodiments can also be provided not only for the carbon dioxide sensor (52) but also for other gas sensors such as an ethylene sensor and a refrigerant leakage sensor which may be used for the transportation container (1) including the air composition adjustment device. The ethylene sensor is a sensor that senses an ethylene concentration in the container, and the refrigerant leakage sensor is a sensor that senses a refrigerant leakage into the container. The oxygen sensor (51) and the carbon dioxide sensor (52) may be of types other than those described in the embodiments.

Although hydrogen sulfide has been described as an example of the corrosive component in the above-described embodiments, the contact reducer (105) of each embodiment can be provided for other corrosive components such as calcium, chlorine, or phosphorus.

In the above-described embodiments, the example where the oxygen sensor (51) which is the target gas sensor is arranged inside the sensor casing (90) has been described, but the contact reducer (105) can be provided even in a case where the sensor casing (90) is not provided.

In the above-described embodiments, one air pump (31) includes the first pump mechanism (31a) and the second pump mechanism (31b). However, the first pump mechanism (31a) and the second pump mechanism (31b) may be two individual air pumps.

In the above-described embodiments, the transfer unit may be configured as a fan.

In each of the above-described embodiments, a single adsorption column is used as each of first and second adsorbers to adsorb and desorb nitrogen. However, the number of adsorption columns forming each adsorber is not limited to one. For example, each adsorber may include three adsorption columns, and a total of six adsorption columns may be used.

The adjuster (34, 35) of the above-described embodiments is not limited to the configuration using the adsorbent such as zeolite, and may have a configuration in which a gas separation membrane having a nitrogen permeability and an oxygen (and carbon dioxide) permeability which are different from each other is used to generate nitrogen-enriched air and oxygen-enriched air and the composition of the inside air is adjusted by concentrated air thereof.

In each of the above-described embodiments, an example of applying the CA system (60) according to the present disclosure to the transportation refrigeration apparatus (10) provided for the container body (2) for marine transportation has been described. However, the application of the CA system (60) according to the present disclosure is not limited thereto. The CA system (60) according to the present disclosure is applicable to adjustment of the composition of the inside air not only in the container for marine transportation, but also in, for example, a container for land transportation, a mere refrigerated warehouse, and a warehouse at a room temperature. The refrigeration apparatus may be a device not for transportation but for cooling an internal space of a stationary storage (a refrigerated warehouse).

The cover unit (100) may include only the cover (101).

While the embodiments and variations thereof have been described above, it will be understood that various changes in form and details may be made without departing from the spirit and scope of the claims. The foregoing embodiments and variations thereof may be combined and replaced with each other without deteriorating the intended functions of the present disclosure.

INDUSTRIAL APPLICABILITY

As can be seen from the foregoing description, the present disclosure is useful for the air composition adjustment device, the transportation refrigeration apparatus, and the transportation container.

EXPLANATION OF REFERENCES

1 Transportation Container
2 Container Body
3 Air Circuit
10 Transportation Refrigeration Apparatus (Refrigeration Apparatus)
20 Refrigerant Circuit
21 Compressor (Component)
22 Condenser (Component)
23 Expansion Valve (Component)
24 Evaporator (Component)
31 Air Pump (Transfer Unit)
34 First Adsorption Column (Adjuster)
35 Second Adsorption Column (Adjuster)
51 Oxygen Sensor (Gas Sensor)
51a Sensor 59 Second Connection Piping (Introduction Path)
60 Air Composition Adjustment Device (Air Composition Adjuster)
90 Sensor Casing
94 Introduction Port (Introduction Path)
94a First Introduction Port
94b Second Introduction Port
100 Cover Unit
101 Cover
105 Adsorbing Member
111 Inflow Path
112 Outflow Path
131 First Tubular Portion
132 Second Tubular Portion
h1 First Hole
h2 Second Hole

The invention claimed is:

1. An air composition adjustment device comprising:
a transfer unit that transfers air;
an adjuster that adjusts the composition of air in a target space;
an air circuit that introduces air into the adjuster by the transfer unit and supplies composition-adjusted air to the target space;
a gas sensor arranged in the target space to measure a component in air; and
a cover unit including a cover that covers around the gas sensor, an inflow path that takes air into the cover, and an outflow path that causes air to flow out from the cover.

2. The air composition adjustment device of claim 1, wherein
an inner diameter of the inflow path- and an inner diameter of the outflow path are 1 mm or more and 4 mm or less.

3. The air composition adjustment device of claim 1, wherein
the outflow path is positioned at an upper portion of the cover.

4. The air composition adjustment device of claim 1, wherein
the inflow path is positioned at a lower portion of the cover.

5. The air composition adjustment device of claim 1, wherein
the gas sensor includes a sensor positioned on a straight line connecting the inflow path and the outflow path together.

6. The air composition adjustment device of claim 1, wherein
the inflow path is formed by a first hole provided in the cover, and
the outflow path is formed by a second hole provided in the cover.

7. The air composition adjustment device of claim 1, wherein
the inflow path is formed by a first tubular portion connected to the cover, and
the outflow path is formed by a second tubular portion connected to the cover.

8. The air composition adjustment device of claim 1, wherein
the gas sensor is configured to generate heat while being turned ON, and
the cover is configured to generate an air flow due to heat generation of the gas sensor.

9. The air composition adjustment device of claim 1, further comprising:
a sensor casing that houses the gas sensor therein,
the sensor casing including an introduction port that introduces air into the sensor casing; and
the cover being arranged between the introduction port and the gas sensor.

10. The air composition adjustment device of claim 9, wherein
the introduction port is arranged below the gas sensor, and
the cover has a portion arranged below the gas sensor.

11. The air composition adjustment device of claim 9, wherein
the introduction port includes a first introduction port that introduces air in the target space into the sensor casing and a second introduction port that introduces air outside the target space into the sensor casing, and
at least one of the first introduction port or the second introduction port is arranged below the gas sensor, and
the cover has a portion arranged below the gas sensor.

12. The air composition adjustment device of claim 1, further comprising:
a contact reducer that reduces contact of a corrosive component in air with the gas sensor,
the contact reducer including an adsorbing member being capable of adsorbing the corrosive component in the air thereto.

13. The air composition adjustment device of claim 12, further comprising:
a sensor casing that houses the gas sensor therein,
the adsorbing member being arranged inside the sensor casing.

14. The air composition adjustment device of claim 12, further comprising:
a sensor casing that houses the gas sensor therein, and and an introduction path that introduces air into the sensor casing, the introduction path being connected to the sensor casing,
the adsorbing member being arranged in the introduction path.

15. The air composition adjustment device of claim 12, further comprising:
a sensor casing that houses the gas sensor therein,
the sensor casing having an introduction port that introduces air into the sensor casing, and
the adsorbing member being arranged in the introduction port.

16. The air composition adjustment device of claim 12, wherein
the adsorbing member is arranged in an inflow portion through which air flows into the air circuit.

17. The air composition adjustment device of claim 12, wherein
the adsorbing member is capable of adsorbing a corrosive component including sulfur or phosphorus.

18. A refrigeration apparatus comprising:
components of a refrigerant circuit that perform a refrigeration cycle; and an air composition adjuster that adjusts the composition of air in a target space,
the refrigerant circuit including an evaporator that cools the air in the target space, and
the air composition adjuster including the air composition adjustment device of claim 1.

19. A transportation container comprising:
a container body configured to transport a fresh item; and
a transportation refrigeration apparatus configured to cool the inside of the container body as a target space, the transportation refrigeration apparatus including the refrigeration apparatus of claim 18.

\* \* \* \* \*